(12) United States Patent
Nakajima et al.

(10) Patent No.: US 10,022,070 B2
(45) Date of Patent: Jul. 17, 2018

(54) INTEGRATED CIRCUIT INCLUDING A DETECTION UNIT FOR DETECTING AN ANGULAR VELOCITY SIGNAL OF A MOVING OBJECT BASED ON A SIGNAL FROM A SENSOR

(71) Applicant: Seiko Epson Corporation, Tokyo (JP)

(72) Inventors: Katsuhito Nakajima, Hachioji (JP); Katsuhiko Maki, Chino (JP); Shunichi Mizuochi, Matsumoto (JP)

(73) Assignee: Seiko Epson Corporation (JP)

( * ) Notice: Subject to any disclaimer, the term of this patent is extended or adjusted under 35 U.S.C. 154(b) by 781 days.

(21) Appl. No.: 14/536,809

(22) Filed: Nov. 10, 2014

(65) Prior Publication Data

US 2016/0161254 A1   Jun. 9, 2016

(30) Foreign Application Priority Data

Nov. 11, 2013   (JP) .................................. 2013-233372

(51) Int. Cl.
*A61B 5/00* (2006.01)
*A61B 5/11* (2006.01)
*G01C 21/20* (2006.01)

(52) U.S. Cl.
CPC ..... *A61B 5/1116* (2013.01); *A61B 2562/0219* (2013.01); *G01C 21/20* (2013.01)

(58) Field of Classification Search
CPC ......... A61B 5/065; A61B 5/11; A61B 5/1116; A61B 5/1126; A61B 5/22; A61B 5/72; A61B 5/721; A61B 5/7225; A61B 5/7271
See application file for complete search history.

(56) References Cited

FOREIGN PATENT DOCUMENTS

| JP | 61-072618 U | 5/1986 |
|---|---|---|
| JP | 05-133762 A | 5/1993 |
| JP | 11-295102 A | 10/1999 |
| JP | 2001-280970 A | 10/2001 |
| JP | 2005-149009 A | 6/2005 |
| JP | 2007-276507 A | 10/2007 |
| JP | 2010-179917 A | 8/2010 |
| JP | 2012-173190 A | 9/2012 |

*Primary Examiner* — Anh Mai
(74) *Attorney, Agent, or Firm* — Harness, Dickey & Pierce, P.L.C.

(57) ABSTRACT

An IC for a sensor includes a detection unit which detects an angular velocity signal of a moving object based on a signal from a sensor element, an AD conversion unit which converts an analog signal from the detection unit into a digital signal, and a posture variation calculating unit which calculates a variation in posture of the moving object during a predetermined period based on the signal from the AD conversion unit.

10 Claims, 17 Drawing Sheets

FIG. 8A
● C REGISTER INITIALIZATION    state_init_creg

| sequence | MULTIPLIER | | | ADDER | | C REGISTER | | | | | | | | |
|---|---|---|---|---|---|---|---|---|---|---|---|---|---|---|
| | X | Y | | A | B | c11 | c12 | c13 | c21 | c22 | c23 | c31 | c32 | c33 |
| #01 | 0 | 0 | | 0 | 1 | C11(n)=1 | | | | | | | | |
| #02 | 0 | 0 | | 0 | 0 | | C12(n)=0 | C13(n)=0 | C21(n)=0 | C22(n)=1 | | | | C33(n)=1 |
| #03 | 0 | 0 | | 0 | 0 | | | | | | C22(n)=0 | C31(n)=0 | C32(n)=0 | |

FIG. 8B
● α MATRIX COMPUTATION    state_alphamatrix

| sequence | MULTIPLIER | | | ADDER | | A REGISTER | | | | | | | | |
|---|---|---|---|---|---|---|---|---|---|---|---|---|---|---|
| | X | Y | | A | B | a11 | a12 | a13 | a21 | a22 | a23 | a31 | a32 | a33 |
| #01 | DOutX | kr | | 0 | 0 | a11(tmp)=oadder | | | | | | | | |
| #02 | DOutY | kr | | PReg | −biasX | | | | | | | | | |
| #03 | DOutZ | kr | | PReg | −biasY | | | | | | | | | |
| #04 | a11 | Ts | | PReg | −biasZ | | | | | | | | | |
| #05 | a22 | Ts | | ~PReg | "1" | a11(n)=0 | | | | | | | | |
| #06 | a33 | Ts | | ~PReg | "1" | | | a13(n)=opout | a21(n)=opout | a22(tmp)=oadder | | | a32(n)=opout | a33(tmp)=oadder |
| #07 | 0 | 0 | | ~PReg | "1" | | | | | a22(n)=0 | a23(n)=oadder | a31(n)=oadder | | a33(n)=0 |
| #08 | 0 | 0 | | 0 | 0 | | a12(n)=oadder | | | | | | | |

FIG. 8C
● exp COMPUTATION (FIRST ORDER)    state_app_exp1

| sequence | MULTIPLIER | | | ADDER | | A REGISTER | | | | | | | | |
|---|---|---|---|---|---|---|---|---|---|---|---|---|---|---|
| | X | Y | | A | B | a11 | a12 | a13 | a21 | a22 | a23 | a31 | a32 | a33 |
| #01 | 0 | 0 | | a11 | 1 | | | | | | | | | |
| #02 | 0 | 0 | | a22 | 1 | a11(n)=oadder | | | | | | | | |
| #03 | 0 | 0 | | a33 | 1 | | | | | a22(n)=oadder | | | | |
| #04 | 0 | 0 | | 0 | 0 | | | | | | | | | a33(n)=oadder |

INTEGRATED CIRCUIT INCLUDING A DETECTION UNIT FOR DETECTING AN ANGULAR VELOCITY SIGNAL OF A MOVING OBJECT BASED ON A SIGNAL FROM A SENSOR

BACKGROUND

1. Technical Field

The present invention relates to an IC for a sensor, a sensor device, an electronic device, and a moving object.

2. Related Art

For an inertial navigation system, a method of computing a posture of a moving object by using an output of an angular velocity sensor is known.

JP-A-2001-280970 discloses a technique of correcting first posture computation, which has a smaller order of Taylor expansion and a relatively large computation frequency, with second posture computation which has a larger order of Taylor expansion and a smaller computation frequency as compared with the first posture computation in order to compute a posture angle with high precision at a high speed.

In JP-A-2001-280970, computation for correction at a low frequency is performed in the second posture computation. According to such posture computation, the number of samples which are not used in the posture computation is large among samples of angular velocity data output from a gyro sensor, and therefore, there is a possibility that correction cannot be performed accurately.

It is known that when a moving object with a large variation in angular velocity in a short time, such as a human, is targeted, accuracy of the posture angle computed by the above posture calculation method deteriorates.

SUMMARY

An advantage of some aspects of the invention is to provide an IC for a sensor which calculates a variation in posture of a moving object without increasing a burden on a CPU on a side of a host which performs overall control for calculating the position of the moving object, and to provide a sensor device, an electronic device, and a moving object which include the same.

(1) An aspect of the invention relates to an IC for a sensor including: a detection unit which detects an angular velocity signal based on a signal from a sensor element; an AD conversion unit which converts an analog signal from the detection unit into a digital signal; and a posture variation calculating unit which calculates a variation in posture of a moving object during a predetermined period based on the signal from the AD conversion unit.

The IC for a sensor according to the aspect of the invention can be used by being connected to a host terminal which calculates a position of the moving object in a second coordinate system (an absolute coordinate system, a moving object coordinate system, or the like) which is different from a first coordinate system (sensor coordinate system), for example. For coordinate conversion, it is necessary to update the posture of the moving object. The posture (angle) of the moving object is obtained by integrating an angular velocity from a gyro sensor. The integral value has higher accuracy as the amount of angular velocity data within an integration period is larger, that is, as an input frequency of the angular velocity data input to the posture variation calculating unit is higher. According to the aspect of the invention, if it is assumed that the input frequency of the angular velocity data input to the posture variation calculating unit is a first frequency f1, for example, the first frequency f1 can be higher than an input frequency (second frequency f2) of the variation in posture and the angular velocity data input to a posture updating unit provided in the host terminal. Therefore, it is possible to suppress degradation of accuracy in integration even if a variation in angular velocity is relatively large as in a case of a moving object which performs walking motion, for example. In addition, the input frequency of the variation in posture which is input to the posture updating unit on the side of the host terminal is the second frequency f2 which is lower than the first frequency f1. Therefore, a burden on a CPU in the host terminal is reduced.

(2) In the aspect of the invention, the posture variation calculating unit may compute $\exp([\alpha_{ib}^{b}(t+\tau_1)]\times)\exp([\alpha_{ib}^{b}(t+2\tau_1)]\times) \ldots \exp([\alpha_{ib}^{b}(t+k\tau_1)]\times)$ where $\tau_1=1/f1$, k is an integer which satisfies $(f1/f2)-1 < k \leq f1/f2$, t represents a time, and $[\alpha_{ib}^{b}(t+n\tau_1)]$ represents a rotation matrix acquired from the angular velocity at a time $t+n\tau_1$ (n is an integer which satisfies $1 \leq n \leq k$).

By computation of performing multiplication k times as in $\exp([\alpha(t+\tau)\times])\exp(([\alpha(t+2\tau)\times] \ldots \exp([\alpha(t+k\tau)]\times))$ using the variation in posture $\exp(([\alpha(t+n\tau_1)]\times)$ for every n-th first cycle $\tau_1$, it is possible to accurately calculate the variation in posture of the moving object. In addition, the first and second cycles $\tau_1$ and $\tau_2$ and the aforementioned first and second frequencies f1 and f2 establish relationships of $\tau_1=1/f1$ and $\tau_2=1/f2$. Therefore, k=f1/f2 is established. In addition, since k is a number of an α matrix which can be multiplied during the period even if f1/f2 is not an integer, an integer k which satisfies $(f1/f2)-1 < k \leq = f1/f2$ can be obtained.

(3) In the aspect of the invention, the IC for a sensor may further include: a control unit which controls the posture variation calculating unit based on a command signal input from the outside.

With such a configuration, the control unit can control the posture variation calculating unit based on the command signal input from the outside, for example, the host terminal, and various kinds of setting for calculating the variation in posture in the IC for a sensor can be arbitrarily set from the outside.

(4) In the aspect of the invention, the control unit may set a start and an end of calculating operation by the posture variation calculating unit based on the command signal.

By setting a start and an end of calculating operation by the posture variation calculating unit based on the command signal as described above, it is possible to set a computation cycle (integration cycle) at the first frequency f1 which is different from the second frequency f2 on the side of the host terminal as described above.

(5) In the aspect of the invention, the IC for a sensor may further include: a command decoder which decodes the command signal input from the outside; and a register in which a value for controlling the posture variation calculating unit is set based on a decoding result of the command decoder.

That is, the aforementioned control unit can be configured of the command decoder and the register.

(6) In the aspect of the invention, the command decoder may set a start and an end of the calculating operation by the posture variation calculating unit in the register based on the command signal.

With such a configuration, it is possible to set the computation cycle (integration cycle) at the first frequency f1 which is different from the second frequency f2 on the side of the host terminal as described above.

(7) In the aspect of the invention, the posture variation calculating unit may be configured of hardware which includes an adder and a multiplier which perform approximating operation of $\exp([\alpha(t+n\tau_1)]\times)$.

With such a configuration, accuracy is not degraded if the calculation of the variation in posture is developed as $\exp([\alpha(t+\tau)+\alpha(t+2\tau)+\alpha(t+3\tau) \ldots +\alpha(t+k\tau)\times]$, and it is possible to perform the computation with relatively high accuracy by computation of $\exp([\alpha(t+\tau)\times])\exp([\alpha(t+2\tau)\times] \ldots \exp([\alpha(t+k\tau)]\times)$. In addition, since the posture variation calculating unit performs the computation at the relatively high first frequency f1 by using the hardware including the adder and the multiplier, the burden on the CPU does not increase.

(8) Another aspect of the invention is directed to a sensor device, an electronic device, and a moving object, each of which includes: a sensor element; and the IC for a sensor according to any one of (1) to (7).

According to the aspect of the invention, it is also possible to calculate the variation in posture of the moving object by the IC for a sensor without increasing the burden on the CPU on the side of the host which performs overall control for calculating the position of the moving object.

BRIEF DESCRIPTION OF THE DRAWINGS

The invention will be described with reference to the accompanying drawings, wherein like numbers reference like elements.

FIG. 8A is a diagram illustrating an initialization operation of a C register, FIG. 8B is a diagram illustrating a matrix computation, and FIG. 8C is a diagram illustrating an exp computing operation.

DESCRIPTION OF EXEMPLARY EMBODIMENTS

Hereinafter, an example of preferred embodiments of the invention will be described with reference to drawings. However, it is a matter of course that the embodiments to which the invention can be applied are not limited to the embodiments which will be described below.

1. System Configuration

Figure 1:
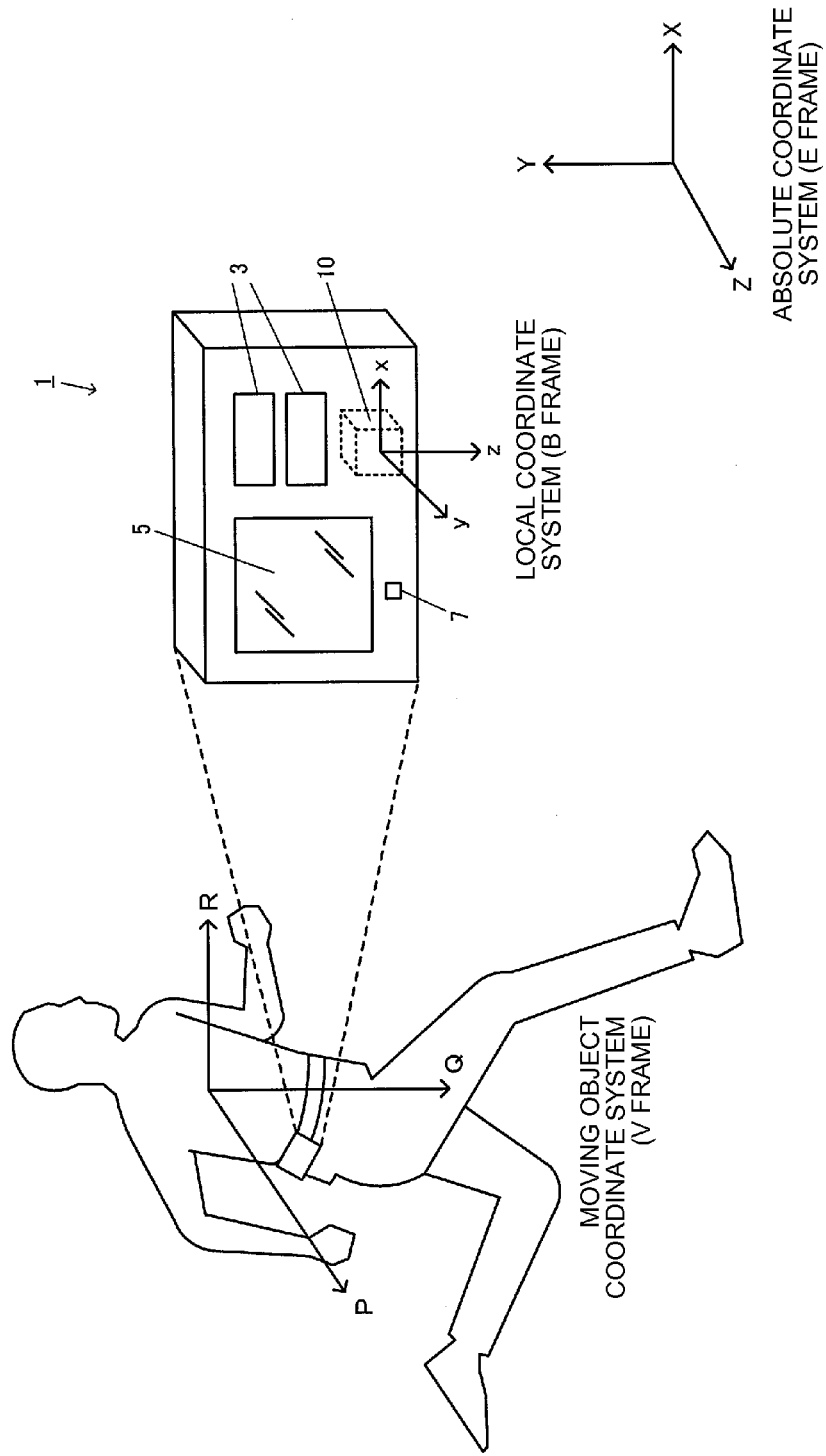
FIG. 1 is a diagram showing a configuration example of an overall system of a position calculating apparatus.

FIG. 1 is a diagram showing a configuration example of an overall system of a position calculating apparatus (electronic device) 1 according to the embodiment. The position calculating apparatus 1 is a small-sized electronic device used by being mounted on a living object or a moving object which moves by using energy of the living body as a power source, for example, on a waist (a right waist or a left waist) of a human, and is a kind of posture calculating apparatus. In addition, the moving object may be a two-legged robot, for example, and can be a robot (moving object) with the position calculating apparatus 1 mounted thereon. The position calculating apparatus 1 includes an operation button 3 as an input device for the moving object to input various operations relating to calculation of a position, a liquid crystal display 5 on which information of the calculated position and the like are displayed, and a speaker 7. In this specification, the living object and the moving object will be collectively referred to as a "moving object".

In the embodiment, at least three kinds of coordinate systems are defined. A first coordinate system is a local coordinate system which is a three-dimensional orthogonal coordinate system (sensor coordinate system) which is associated with an inertial measurement unit (IMU) 10 provided in the posture calculating apparatus 1. In this specification, the local coordinate system will also be referred to as a body (B) frame in which a detection axis of an inertial sensor is represented by a right-handed system. In the embodiment, three axes of the local coordinate system will be described as an x axis, a y axis, and a z axis.

A second coordinate system is a three-dimensional orthogonal coordinate system (absolute coordinate system) which is a coordinate system defining a moving space of the moving object. In this specification, the absolute coordinate system will also be referred to as an absolute (A) frame. The A frame is defined as a North East Down (NED) coordinate system (N frame) which is known as a north east down coordinate system or an Earth Centered Earth Fixed (ECEF) coordinate system (E frame) which is known as an earth centered earth fixed coordinate system, for example. In the embodiment, three axes of the absolute coordinate system will be described as an X axis, a Y axis, and a Z axis.

The second coordinate system may be a three-dimensional orthogonal coordinate system (moving object coordinate system) which is associated with the moving object. In this specification, the moving object coordinate system will also be referred to as a vehicle (V) frame. In the embodiment, a front-back direction in which the front side of the moving object corresponds to a positive side is represented as a roll axis (R axis), a left-right direction in which the right side corresponds to a positive side is represented as a pitch axis (P axis), and an upper-lower direction in which the vertically lower side corresponds to a positive side is represented as a yaw axis (Q axis).

A third coordinate system is an inertial coordinate system (not shown) which is a three-dimensional orthogonal coordinate system as a reference for the IMU 10 to perform detection. In this specification, the third coordinate system will also be referred to as an inertial (I) frame. The I frame is a coordinate system in which the center of the earth is regarded as an origin and the rotational axis of the earth is regarded as an axis. The rotation of the earth is not taken into consideration. In the embodiment, three axes of the inertial coordinate system will be described as an L axis, an M axis, and an N axis. In the embodiment, the N axis corresponds to the rotation axis of the earth.

Figure 2:
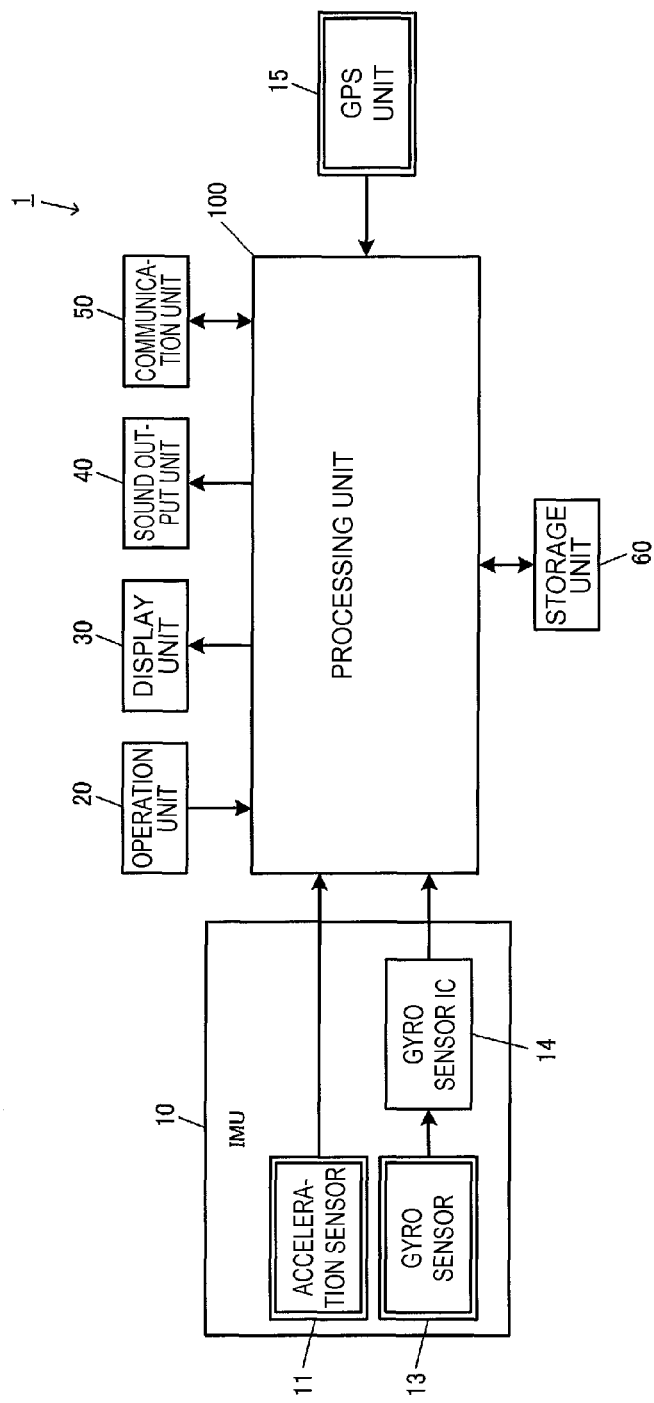
FIG. 2 is a functional block diagram of the position calculating apparatus.

The IMU 10 is a sensor device which is mounted on the position calculating apparatus 1 and is known as an inertial navigation unit. The IMU 10 includes an acceleration sensor 11, a gyro sensor 13, and a gyro sensor IC (an IC for the sensor) 14 including a posture variation calculating unit as shown in FIG. 2. As shown in FIG. 1, the z axis of the IMU 10 is an axis in the vertical direction.

The acceleration sensor 11 detects an acceleration vector for three axes (the x axis, the y axis, and the z axis) in the local coordinate system with respect to the respective axes (the L axis, the M axis, and the N axis) in the corresponding inertial coordinate system. As the acceleration sensor 11, a micro electro mechanical system (MEMS) sensor is used, for example. A value measured by the acceleration sensor 11 corresponds to an acceleration of the moving object which is measured in the local coordinate system.

The acceleration sensor 11 detects an acceleration vector of the moving object for the three axes (the x axis, the y axis, and the z axis) in the local coordinate system. As the acceleration sensor 10, a micro electro mechanical system (MEMS) sensor is used, for example. A value measured by the acceleration sensor 10 corresponds to an acceleration of the moving object which is measured in the local coordinate system.

In this specification, an acceleration and a velocity represent an acceleration and a velocity (that is, an acceleration vector and a velocity vector) obtained by taking a direction and a size into consideration in principle unless otherwise particularly noted.

The gyro sensor 13 detects angular velocity (hereinafter, referred to as a "local coordinate angular velocity") for the three axes (the x axis, the y axis, and the z axis) of the same local coordinate system as that of the acceleration sensor 11 provided in the position calculating apparatus 1 with respect to the respective axes (the L axis, the M axis, and the N axis) of the corresponding inertial coordinate system.

A global positioning system (GPS) unit 15 shown in FIG. 2 is a unit which receives a GPS satellite signal transmitted from a GPS satellite as a kind of a satellite for position measurement and calculates a position and a velocity vector of the moving object by using the GPS satellite signal. Since the method of calculating the position and the velocity vector by using the GPS is known in the related art, a detailed description will be omitted.

The position calculating apparatus 1 further includes a processing unit (host terminal) 100, an operation unit 20 including the operation button 3 shown in FIG. 1, a display unit 30 including the liquid crystal display 5 shown in FIG. 1, a sound output unit 40 including the speaker 7 shown in FIG. 1, a communication unit 50, and a storage unit 60.

The processing unit 100 collectively controls the respective components in the position calculating apparatus 1 in accordance with various programs such as a system program stored on the storage unit 60.

2. Gyro Sensor IC and Processing Unit

Figure 3:
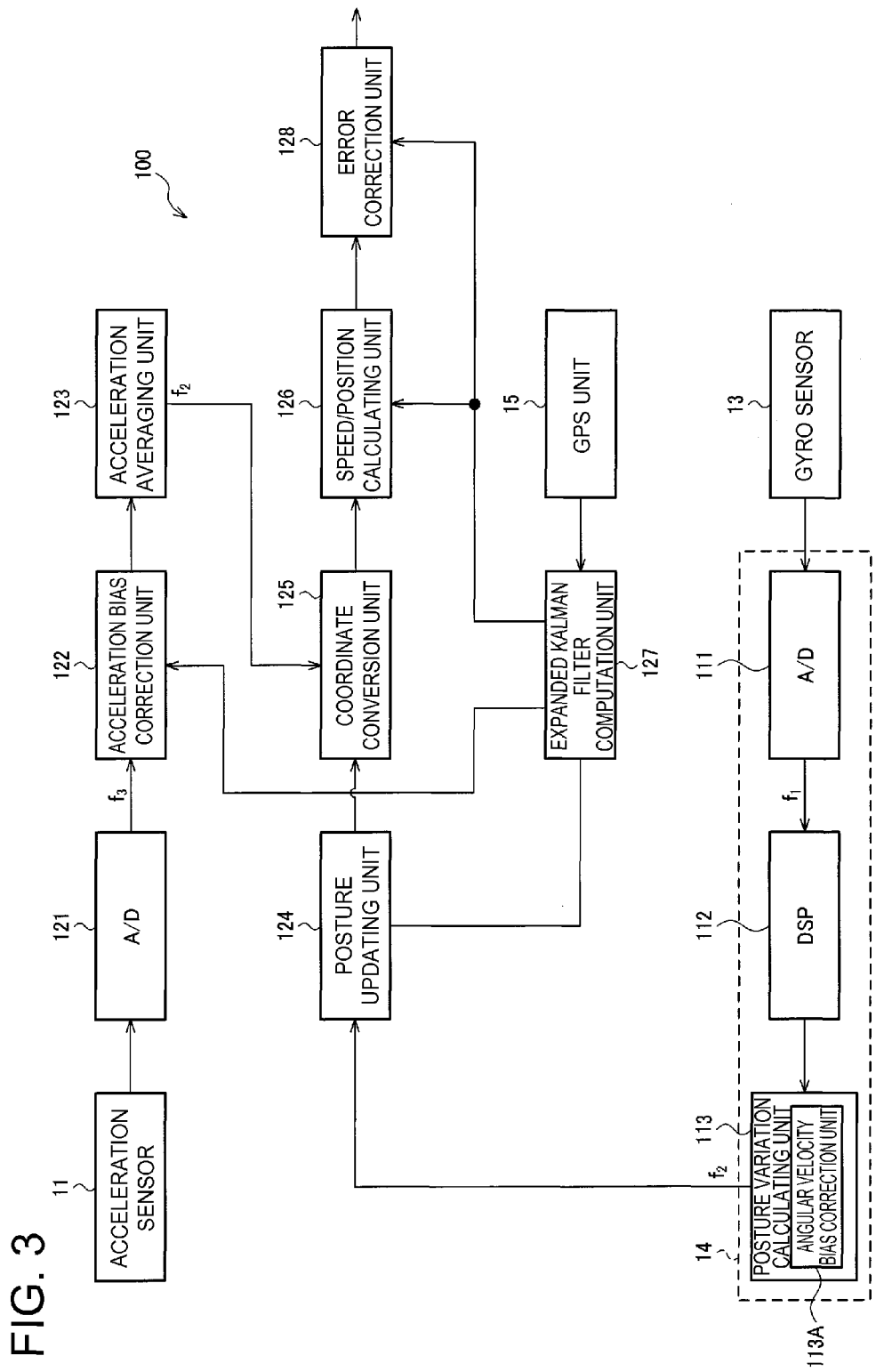
FIG. 3 is a block diagram of a gyro sensor IC and a processing unit.
Figure 4:
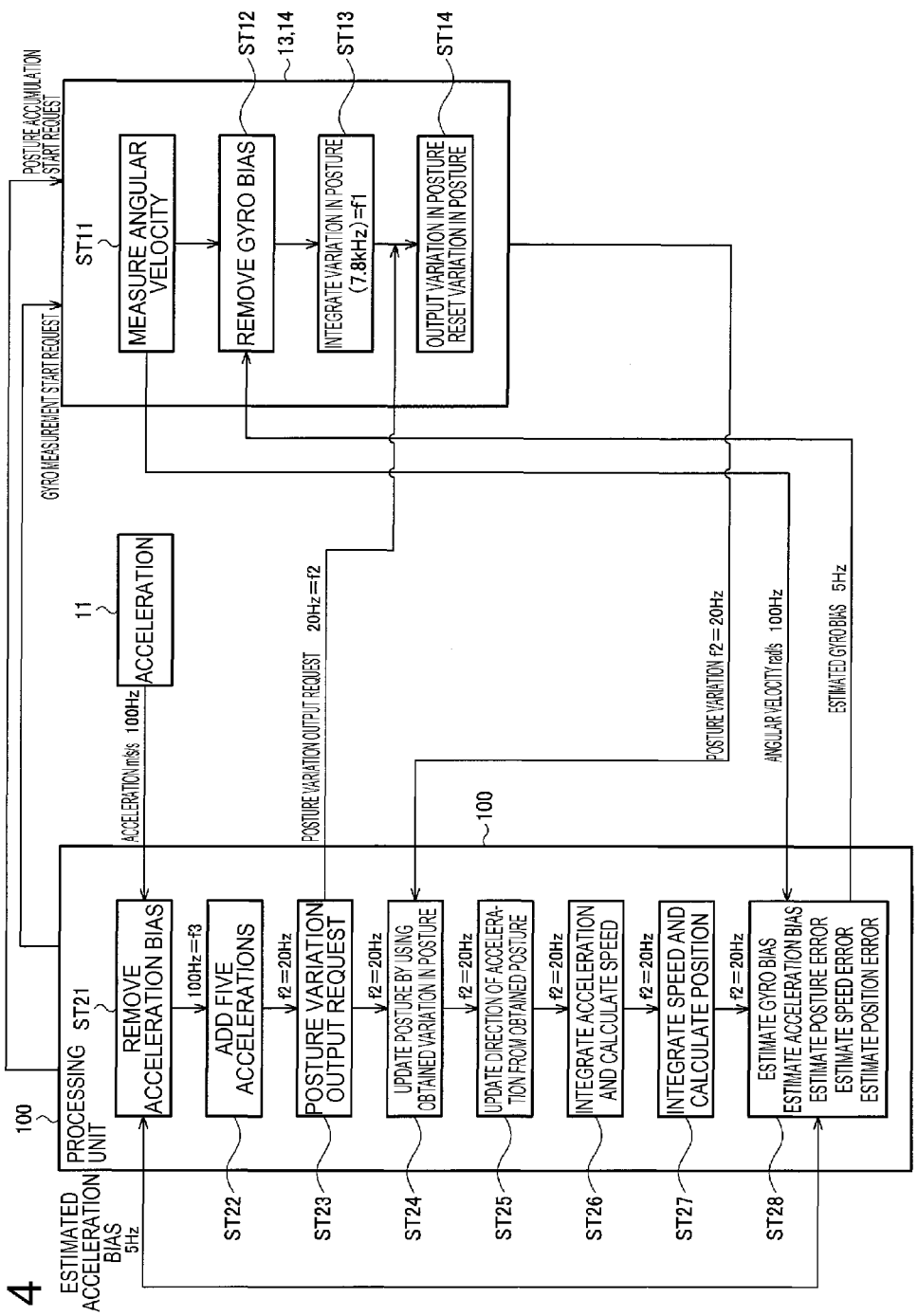
FIG. 4 is a flowchart showing operations of the functional block shown in FIG. 3.

FIG. 3 is a block diagram showing main functional blocks of the gyro sensor IC 14 and the processing unit 100. FIG. 4 shows sequence operations of the functional blocks shown in FIG. 3. In the embodiment, functions of the position calculating apparatus are realized by at least a posture variation calculating unit 113 and a posture updating unit 124 in the configuration which will be described below. The posture calculating apparatus may further include at least one of the gyro sensor 13 or the gyro sensor IC 14, the acceleration sensor 11, and a coordinate conversion unit 125.

In FIGS. 3 and 4, the gyro sensor IC 14 includes an A/D converter 111 which samples the angular velocity detected by the gyro sensor 13 at the first frequency f1 (f1=7.81 kHz, for example) and A/D converts the angular velocity, a digital signal processor (DSP) 112 which performs digital signal processing such as digital filtering, and the posture variation calculating unit 113 which calculates a variation in posture of the moving object based on the angular velocity from the DSP 112. The posture variation calculating unit 113 includes a gyro bias correction unit 113A which corrects a bias of the angular velocity. The posture variation calculating unit 113 calculates a variation in posture of the moving object based on the angular velocity input from the DSP 112 at the first frequency f1.

As shown in FIG. 4, an angular velocity is measured by the gyro sensor 13 (ST11). The posture variation calculating unit 113, to which the angular velocity is input via the A/D converter 111 and the DSP 112, removes a gyro bias in the gyro bias correction unit 113A first (ST12). The posture variation calculating unit 113 integrates the angular velocity input from the DSP 112 at the first frequency f1 over a period (second period τ2) defined by the second frequency f2 (f2=20 Hz, for example) based on a posture output request from the processing unit 100 and calculates a variation in posture of the moving object (ST13). The posture variation calculating unit 113 resets the variation in posture after outputting the calculated variation in posture (ST14).

The processing unit 100 includes an A/D converter 121 which samples an acceleration detected by the acceleration sensor 11 at a third frequency f3 (f3=100 Hz, for example) and A/D converts the acceleration, an acceleration bias correction unit 122 which corrects a bias of the acceleration, and an acceleration averaging unit 123 which averages m accelerations (m is an integer which is equal to or greater than two and satisfies (f3/f2)−1<m≤f3/f2. m=5, for example) sampled at the third frequency f3 and outputting the acceleration at the second frequency f2 as an output frequency, as shown in FIG. 3. In the processing unit 100, a bias is removed from the acceleration from the acceleration sensor 11 after the A/D conversion (ST21), and five accelerations are averaged (S22) as shown in FIG. 4.

The processing unit 100 further includes a posture updating unit 124 which updates the posture of the moving object based on the variation in posture, which is output from the posture variation calculating unit 113 at the second frequency f2, as shown in FIG. 3. The posture variation calculating unit 113 calculates a variation in posture of the moving object based on the angular velocity input from the DSP 112 at the first frequency f1. The posture variation calculating unit 113 outputs the variation in posture to the posture updating unit 124 at the second frequency f2 as an output frequency in response to a request from the posture updating unit 124. As shown in FIG. 4, the processing unit 100 outputs the posture variation request to the posture variation calculating unit 113 at the second frequency f2 (ST23) and updates the posture by using the variation in posture obtained from the posture variation calculating unit 113 (ST24).

The processing unit 100 further includes a coordinate conversion unit 125. The coordinate conversion unit 125 calculates an acceleration (hereinafter, referred to as a "second coordinate system acceleration") of the moving object after coordinate conversion from the first coordinate system to the second coordinate system, based on the posture of the moving object updated by the posture updating unit 124 at the second frequency f2 and the acceleration input at the second frequency f2. As shown in FIG. 4, the processing unit 100 updates the direction of the acceleration of the moving object based on the obtained posture (ST25).

The processing unit 100 further includes a velocity/position calculating unit 126. As shown In FIG. 4, the velocity/position calculating unit 126 integrates the second coordinate system acceleration output from the coordinate conversion unit 125 and calculates a speed and a position of the moving object in the second coordinate system (ST26 and ST27).

As described above, the position calculating apparatus 1 calculates the position of the moving object which performs walking motion in the second coordinate system (the absolute coordinate system, the moving object coordinate system, or the like). For the coordinate conversion from the first coordinate system to the second coordinate system, the posture of the moving object updated by the posture updating unit 124 is used. The posture (angle) of the moving object is obtained by updating the previous posture with the use of the variation in posture obtained by the posture variation calculating unit 113 integrating the angular velocity detected by the gyro sensor 13. As the amount of data on the angular velocities (the number of samples) during the integration period is larger, that is, as the frequency (input frequency) of the angular velocity input to the posture variation calculating unit 113 is higher, accuracy of the calculated posture is higher. In the embodiment, the frequency of the angular velocity input to the posture variation calculating unit 113 is the first frequency f1, which is higher than the posture variation frequency (second frequency f2) input to the posture updating unit 124. Therefore, it is possible to suppress degradation of integration accuracy as compared with a case where integration is performed at the second frequency f2, even when the variation in angular velocity is relatively large as in a case of the moving object which performs walking motion. In contrast, the posture variation frequency input to the posture updating unit 124 is the second frequency f2 which is lower than the first frequency f1. Therefore, the burden on the CPU in the computation after the updating of the posture is reduced as compared with the case where the variation in posture is input to the posture updating unit 124 at the first frequency f1.

The processing unit 100 further includes an extended Kalman filter computation unit 127 and an error correction unit 128. The extended Kalman filter computation unit 127 estimates errors in a position, a velocity, and an orientation by the extended Kalman filter by using posture data output from the posture updating unit 124, position data and speed data output from the velocity/position calculating unit 126, position measurement data (the position, the speed, and the orientation) from the GPS sensor 15, and acceleration after correction of the acceleration bias by the acceleration bias correction unit 122 as shown in FIG. 4 (ST28). In addition, the extended Kalman filter computation unit 127 estimates the gyro bias and the acceleration bias and outputs the gyro bias and the acceleration bias to the acceleration bias correction unit 122 and the gyro bias correction unit 113A. By using the errors of the position, the speed, and the posture estimated by the extended Kalman filter computation unit 127, the position, the velocity, and the posture of the moving object are corrected by the error correction unit 128. Information from the error correction unit 128 corresponds to an output from the processing unit 100.

3. Specific Example of Gyro Sensor IC

Figure 5:
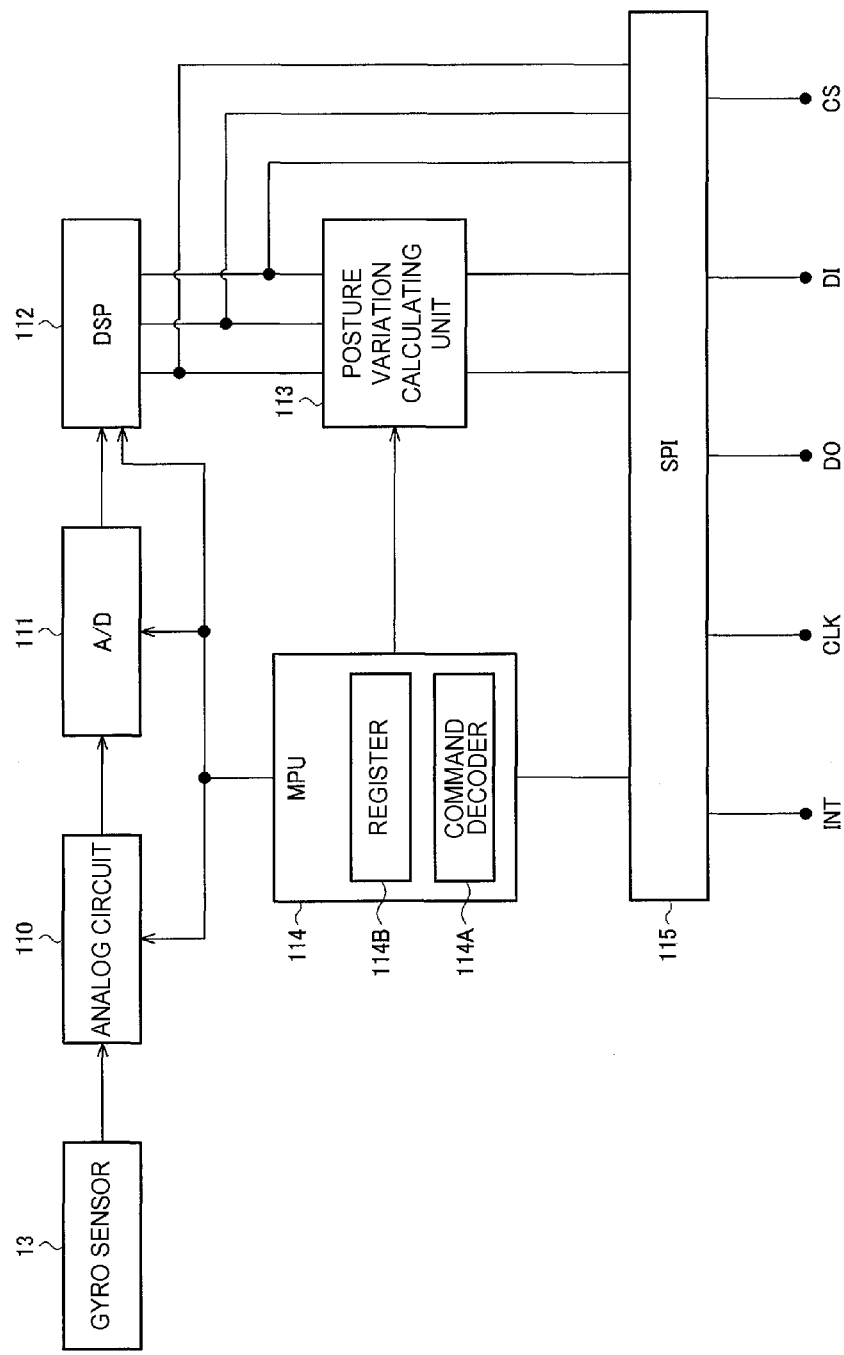
FIG. 5 is a block diagram showing a detail of the gyro sensor IC.

FIG. 5 shows a specific example of the gyro sensor IC 14. In FIG. 5, an analog circuit 110, an MPU (control unit) 114, and a serial peripheral interface (SPI) 115 are provided in addition to the configuration shown in FIG. 3.

The analog circuit 110 Q-V converts and amplifies an output from the gyro sensor 13. The MPU 114 controls the analog circuit 110, the A/D converter 111, the DSP 112, the posture variation calculating unit 113, and the SPI 115 based on command/data input from the SPI 115. Therefore, the MPU 114 includes a command decoder 114A and a register 114B. Various kinds of control data is stored on the register based on a command decoded by the command decoder 114A, and the respective components in the gyro sensor IC 14 are controlled based on the control data. The SPI 115 includes a chip select terminal CS connected to the processing unit 100, a data-in terminal DI, a data-out terminal DO, a clock terminal CLK, and an interruption terminal INT. To the MPU 114, a request command is input from the posture updating unit 124 of the processing unit 100 via the SPI 115. The request command is a command for requesting an output of a variation in posture from the posture variation calculating unit 113 at the second frequency f2 as an output frequency. The request decoded by the command decoder 114A is provided to the posture variation calculating unit 113 via the register 114B, and the variation in posture is output. An interruption output may be output from the interruption terminal INT to the processing unit 100 at the cycle of the second frequency f2, and a command (request signal) for requesting an output of the variation in posture may be issued at the time of occurrence of the interruption.

As control values set in the register 114B by a writing (W) command decoded by the command decoder 114A, it is possible to exemplify an approximation function order, a bias updating timing, an angular velocity conversion (LSB→rad/s) coefficient, a DRDY output timing, posture calculation start/stop, and a bias estimated value writing. In addition, it is possible to read a result of computing the variation in posture in accordance with a reading (R) command decoded by the command decoder 114A. The posture variation computation start/stop timing can be made to coincide with the second cycle $\tau_2$ ($\tau_2=1/f2$) of the second frequency f2.

As control values set in the register 114B by a writing (W) command decoded by the command decoder 114A, it is possible to exemplify an approximation function order SelApp, a bias updating timing, an angular velocity conversion (quantization unit LSB→rad/s) coefficient, an INT output timing, posture variation computing start/stop, and a bias estimated value writing. In addition, it is possible to read a result of computing the variation in posture in accordance with a reading (R) command decoded by the command decoder 114A. The posture variation computation start/stop timing can be made to coincide with the second cycle $\tau_2$ (=1/f2) of the second frequency f2.

Here, an example of the computation at the posture variation calculating unit 113, the posture updating unit 124, and the coordinate conversion unit 125 will be represented as the following Equation (1).

$$C_b^e(t+\tau_2) = C_b^e(t)C_{change} - \Omega_{ie}^e C_b^e(t)\tau_2 \qquad (1)$$

In this specification, a coordinate transformation matrix will be represented by a capital "C". In each coordinate transformation matrix, a subscript represents a coordinate system before the coordinate conversion, and a superscript represents a coordinate system after the coordinate conversion. For example, "$C_b^e$" represents a coordinate transformation matrix obtained by coordinate conversion from the local coordinate system (B frame) to the absolute coordinate system (E frame).

The left side of Equation (1) represents a posture at a time $t+\tau_2$, c(t) represents a rotation matrix of a posture at a time t. $C_{change}$ represents a variation in posture during a period from the time t to the time $t+\tau_2$. A minus item in the right side of Equation (1) represents an influence of the rotation of the earth. The influence of the rotation of the earth may be omitted.

$C_{change}$ in Equation (1) can be represented by the following Equation (2).

$$C_{change} = \exp([\alpha_{ib}^b(t+\tau_1)]\times)\exp([\alpha_{ib}^b(t+2\tau_1)]\times) \ldots \exp([\alpha_{ib}^b(t+k\tau_1)]\times) \qquad (2)$$

In Equation (2), $\tau_1 = 1/f1$, and k is an integer which satisfies (f1/f2)−1<k≤f1/f2. In this specification, d-th power of e=2.781 . . . of a natural logarithm will be represented as "exp(d)" (d is an arbitrary numerical value, a matrix, an equation, or the like). In this specification, $\exp([\alpha(t+n\tau_1)]\times)$ will be referred to as a coordinate transformation matrix. Equation (2) means that a variation in the posture for every second cycle $\tau 2$ is calculated by multiplying a total of k coordinate transformation matrixes calculated at an interval of the first cycle $\tau_1$ during the period of the second cycle $\tau 2$.

$\alpha(t+n\tau_1)$ in Equation (2) is a matrix obtained from the angular velocity, and the following Equation (3) is established. Here, n is an integer which satisfies 1≤n≤k.

$$\alpha_{ib}^b(t+n\tau_1) = \omega_{ib}^b(t+n\tau_1)\tau_i \qquad (3)$$

The right side of Equation (3) is a rotation angle between the I frame and the B frame at a time $(t+n\tau_1)$, which is expressed in the B frame, and corresponds to an angular velocity obtained by the detection value of the gyro sensor 13. Therefore, the matrix $([\alpha(t+n\tau_1)]\times)$ in the right side of Equation (2) is a matrix which can be obtained from the angular velocity, and the following Equations (4-1) and (4-2) are obtained.

$$([\alpha_{ib}^b(t+n\tau_1)]\times) = \begin{bmatrix} 0 & -\omega_{ibn}^b(1,3)\cdot\tau_1 & \omega_{ibn}^b(1,2)\cdot\tau_1 \\ \omega_{ibn}^b(1,3)\cdot\tau_1 & 0 & -\omega_{ibn}^b(1,1)\cdot\tau_1 \\ -\omega_{ibn}^b(1,2)\cdot\tau_1 & \omega_{ibn}^b(1,1)\cdot\tau_1 & 0 \end{bmatrix} \qquad (4\text{-}1)$$

$$\begin{bmatrix} \omega_{ib}^b(1)(t+n\tau_1) \\ \omega_{ib}^b(2)(t+n\tau_1) \\ \omega_{ib}^b(3)(t+n\tau_1) \end{bmatrix} = \begin{bmatrix} (\text{angular velocity of } x \text{ axis at time } t+n\tau_1) - \\ (\text{gyro bias of } x \text{ axis}) \\ (\text{angular velocity of } y \text{ axis at time } t+n\tau_1) - \\ (\text{gyro bias of } y \text{ axis}) \\ (\text{angular velocity of } z \text{ axis at time } t+n\tau_1) - \\ (\text{gyro bias of } z \text{ axis}) \end{bmatrix} \qquad (4\text{-}2)$$

As shown by Equation (4-2), the respective elements in the right side of Equation (4-1) are values obtained by multiplying values obtained by correcting the values of the respective axis, which are detected by the gyro sensor at the time $(t+n\tau_1)$, by using the gyro bias by the first cycle $\tau_1$.

Here, it is possible to use first to third-order approximation shown by the following Equations (5) to (7) for the computation of $\exp(\alpha)$.

$$\exp([\alpha_{ib}^b(t)]\times) = \begin{bmatrix} 1 & 0 & 0 \\ 0 & 1 & 0 \\ 0 & 0 & 1 \end{bmatrix} + ([\alpha_{ib}^b(t)]\times) \qquad (5)$$

$$\exp([\alpha_{ib}^b(t)]\times) = \begin{bmatrix} 1 & 0 & 0 \\ 0 & 1 & 0 \\ 0 & 0 & 1 \end{bmatrix} + ([\alpha_{ib}^b(t)]\times) + \frac{([\alpha_{ib}^b(t)]\times)^2}{2} \qquad (6)$$

$$\exp([\alpha_{ib}^b(t)]\times) = \begin{bmatrix} 1 & 0 & 0 \\ 0 & 1 & 0 \\ 0 & 0 & 1 \end{bmatrix} + ([\alpha_{ib}^b(t)]\times) + \frac{([\alpha_{ib}^b(t)]\times)^2}{2} + \frac{([\alpha_{ib}^b(t)]\times)^3}{6} \qquad (7)$$

Figure 6:
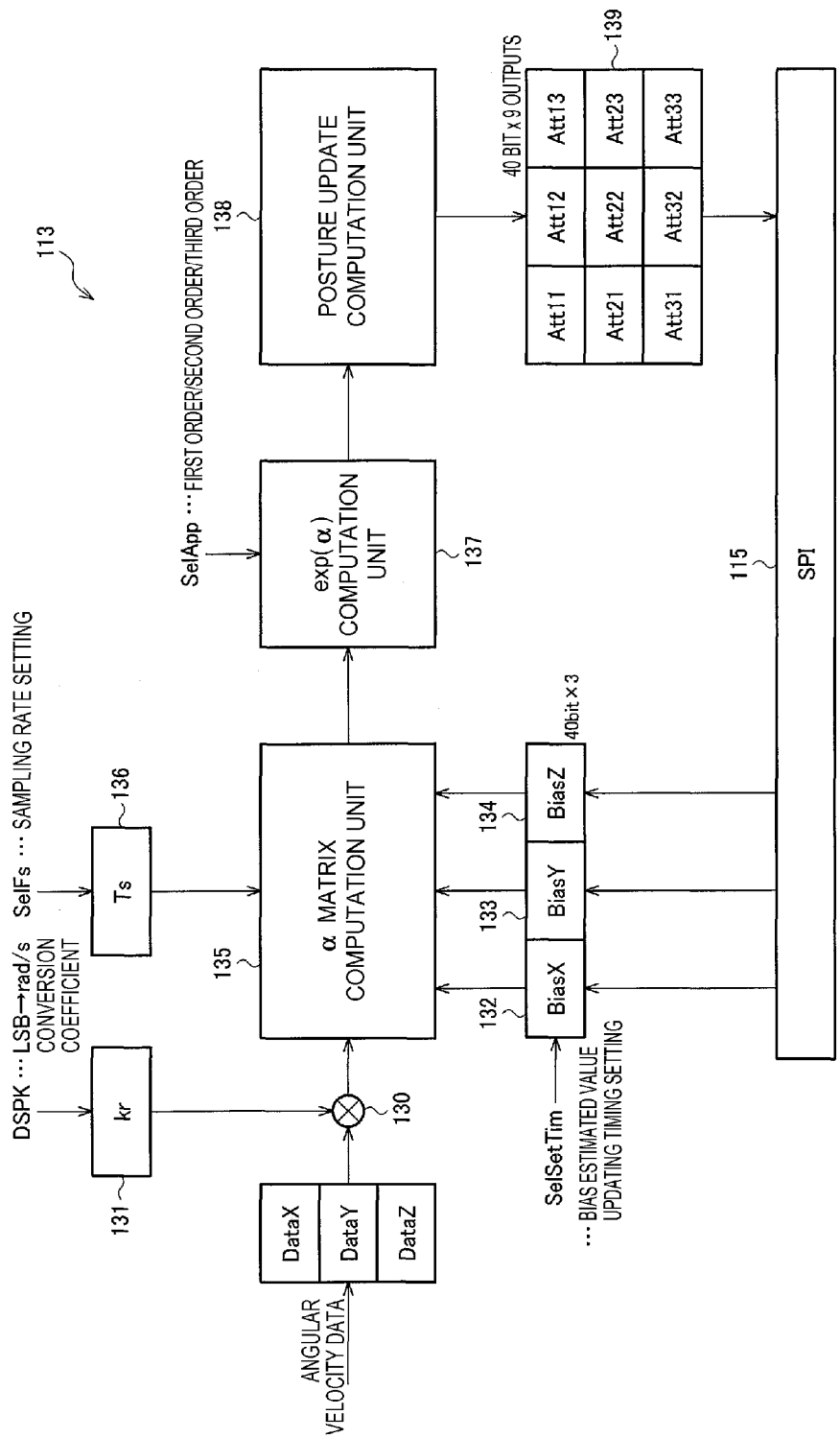
FIG. 6 is a functional block diagram of a posture variation calculating unit in the gyro sensor IC.

FIG. 6 is a functional block diagram of the posture variation calculating unit 113. In addition, registers 131 to 134, 136, and 139 shown in FIG. 6 are specific examples of the register 114B shown in FIG. 5B. To a multiplier 130 shown in FIG. 6, data on the angular velocity input from the gyro sensor 13 (hereinafter, referred to as "angular velocity data") is input. The multiplier 130 converts the angular velocity into rad/s by multiplying the angular velocity data by a coefficient kr of the register 131. The coefficient stored on the register 131 can be stored based on the writing command of the command decoder 114A shown in FIG. 5. The registers 132 to 134 stores a bias correction value (negative value) of Equation (4-2), and the bias correction value is subtracted from the angular velocity by the adder in an α matrix computation unit 135. The adder corresponds to the gyro bias correction unit 113A. The bias correction value is set at a predetermined timing in the registers 132 to 134 by the extended Kalman filter computation unit 127 via the SPI 115. The α matrix computation unit 135 performs matrix computation of Equation (4-1).

By the exp(α) computation unit 137, the approximation computation in any of Equations (5) to (7) is selected with a control signal SelApp set in the register (not shown) based on the writing command of the command decoder 114A shown in FIG. 5, and the approximation computation in any of Equations (5) to (7) is performed. The posture variation updating unit 138 stores, on the register 139, a result of multiplying the latest posture variation data from the exp(α) computation unit 137 by variations in the past according to Equation (2). The posture variation data stored on the register 139 is a 3×3 matrix and corresponds to $C_{change}$ in Equation (2). $C_{change}$ in Equation (2) is sent as an output of 40 bits×9, for example, to the posture updating unit 124 via the SPI 115 in response to a request (command signal) from the posture updating unit 124.

4. Posture Variation Calculating Unit Configured of Hardware

Figure 7:
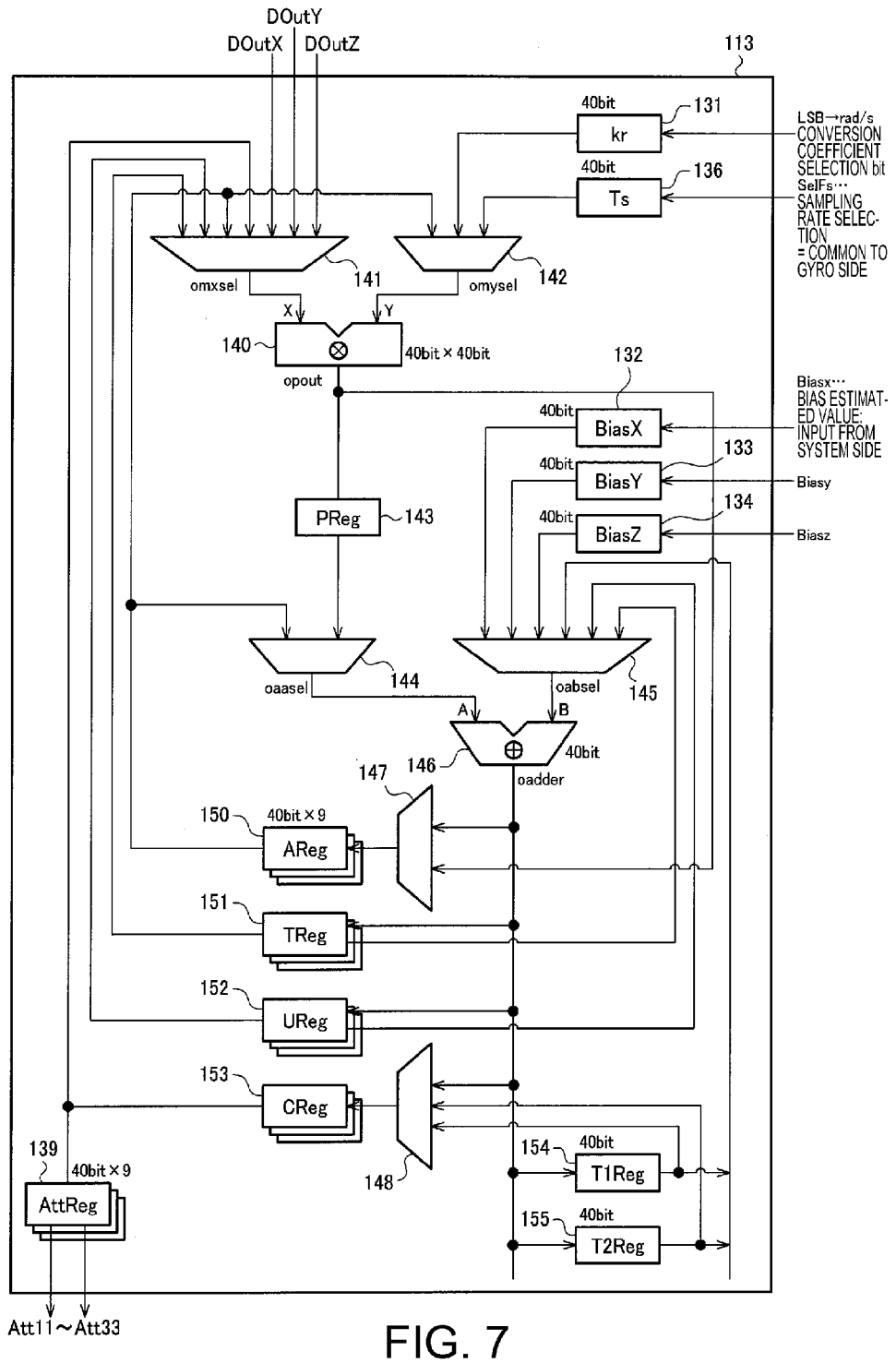
FIG. 7 is a hardware configuration diagram of the posture variation calculating unit.

FIG. 7 is a circuit diagram showing an example in which the posture variation calculating unit 113 is configured of hardware. In FIG. 7, selectors 141, 142, 144, 145, 147, and 148 which select register outputs or the like, registers 143 and 150 to 155, a multiplier 140, and an adder 146, which realize functions of the α matrix computation unit 135 and the exp(α) computation unit 137 shown in FIG. 6 as hardware, are provided. The registers 131 to 134 and 136 shown in FIG. 7 are also specific examples of the register 114B shown in FIG. 5.

Initialization of the C register 153, α matrix computation, and a computation operation based on a first-order approximation represented by Equation (5) from among the operations of the posture variation calculating unit 113 shown in FIG. 6 are shown in FIGS. 8A to 8C and 9. If a posture variation accumulating start request command is input from the system (processing unit 100) in Step 1 (ST1) in FIG. 9, a variation in posture which was calculated in the past and is stored (held) on the C register 153 is reset (deleted) (ST2). Specifically, an initialization operation of the C register 153 shown in FIG. 7 is started as shown in FIG. 8A. By setting a constant 1 or 0 in X and Y terminals of the multiplier 140 and A and B terminals of the adder 146 in procedures (the sequence in FIG. 8A, the same is true to the description below) 1 to 3, regions c11, c22, and c33 in the C register 153 are set to 1, and other regions are set to 0.

Figure 9:
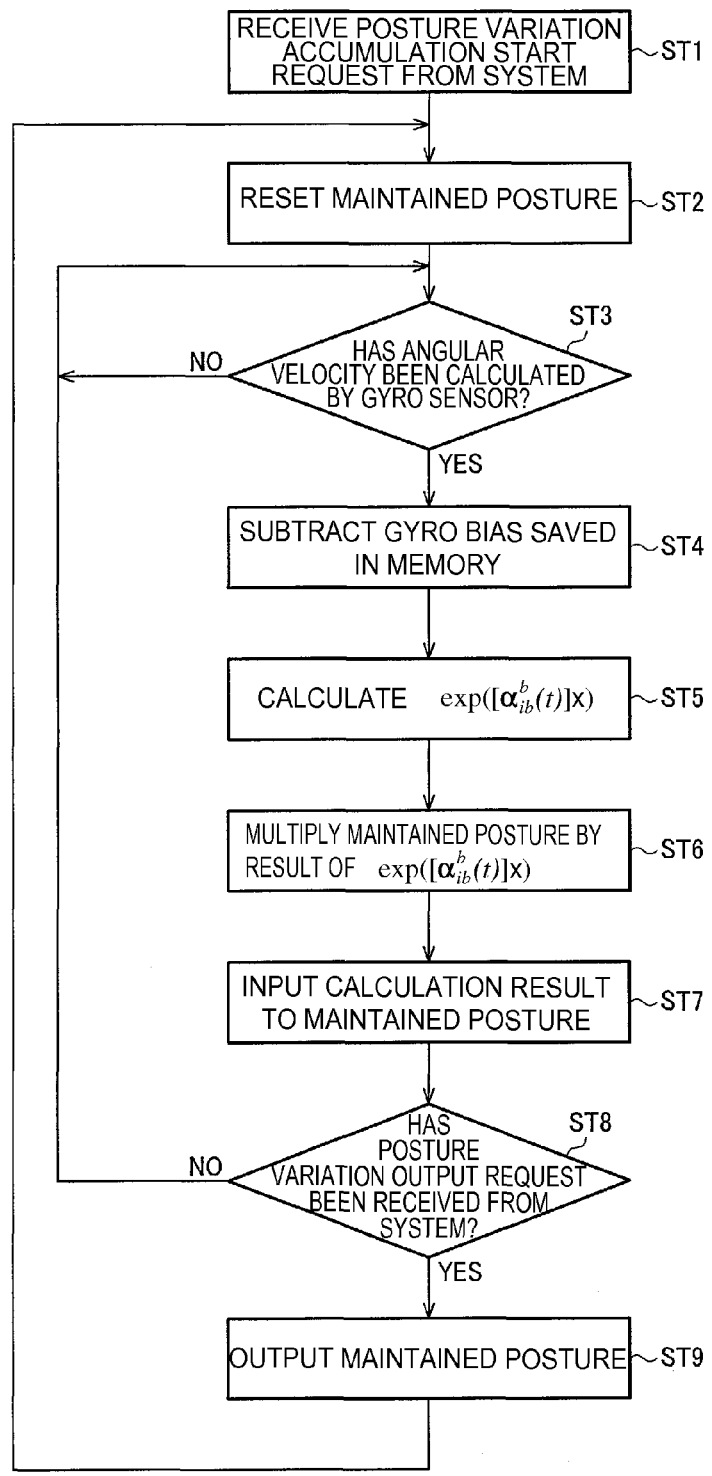
FIG. 9 is a flowchart showing an integration operation of a variation in posture by the posture variation calculating unit.

In Step 3 in FIG. 9, it is determined whether or not an angular velocity has been input. If the angular velocity has been input (YES in ST3), ST4 and ST5 in FIG. 9 are performed. That is, FIG. 8B shows a procedure of the α matrix computation represented by Equation (4) executed by the α matrix computation unit 135 shown in FIG. 6 by using the hardware shown in FIG. 7. Bias correction of the angular velocity data is performed in the procedures 1 to 4 (ST4 in FIG. 9), the matrix computation of Equation (4) is performed in procedures 4 to 7 (ST5 in FIG. 9), and a 3×3 matrix is stored in nine regions a11 to a33 in the A register 150 in procedures 5 to 8. In FIG. 8B, the regions in the A register 150 satisfy a11=a22=a33=0, and an output opout of the multiplier 140 or an output oadder of the adder 146 at a timing shown in FIG. 8B is stored in the other regions a12, a13, a21, a23, a31, and a32.

Next, ST6 in FIG. 9 is performed. FIG. 8C shows a procedure of the exp(α) computation based on the first-order approximation represented by Equation (5) executed by the exp (α) computation unit 137 shown in FIG. 6 by using the hardware shown in FIG. 7. In FIG. 8C, an output oadder of the adder 146 at a timing shown in FIG. 8C is stored on the regions a11, a22, and a33 in the A register 150 (ST7 in FIG. 9).

The posture variation calculating operation shown in FIGS. 8A to 8C is repeatedly performed at the first cycle $\tau_1=1/f1$ on the angular velocity data input at the first frequency f1=7.81 kHz. Therefore, it is determined whether or not a posture variation output request has been provided from the system (processing unit 100) as shown in ST8 in FIG. 9. ST3 to ST7 in FIG. 9 are repeated as long as the answer of ST8 in FIG. 9 is NO. If it is determined that the output request (command signal) has been provided, the posture variation data is sent to the posture updating unit 124 in the processing unit 100 via the C register 153 and an Att register 139 (ST9). In addition, a T register 151, a U register 152, a T1 register 154, a T2 register 155, and the like can be used for second-order and third-order approximation calculation. It is also possible to handle fourth or more order approximation calculation by further adding registers. In addition, the first frequency f1=7.81 kHz is an example, and computation at a higher frequency can also be performed.

The velocity/position calculating unit 126 in FIG. 3 uses a current variation in posture obtained by Equation (2) to calculate the current posture by Equation (1). Then, the following Equation (8) is computed based on the current posture, the posture obtained in the past, and the acceleration detected by the acceleration sensor 11, and acceleration in the E frame is obtained. In addition, $f_{ib}^{b}(t+\tau_2)$ represents an acceleration at a time $t+\tau_2$ and obtained by expressing, in the B frame, an acceleration in the B frame with respect to the I frame at the time $t+\tau_2$.

$$f_{ib}^e(t+\tau 2) \approx \frac{1}{2}(C_b^e(t) + C_b^e(t+\tau 2))f_{ib}^b(t+\tau 2) \qquad (8)$$

Next, the acceleration obtained by Equation (8) and the velocity obtained in the past are used to compute the following Equation (9), and a velocity in the E frame is obtained. $v_{eb}^{e}(t)$ represents, in the E frame, a speed in the B frame with respect to the E frame at the time t. In the third and fourth items in the right side of Equation (9), the influences of the force of gravity and the rotation of the earth are taken into consideration.

$$v_{eb}^e(t+\tau_i) = v_{eb}^e(t) + [f_{ib}^e(t+\tau_i) + g_b^e - 2\Omega_{ie}^e v_{eb}^e(t)]\tau_i \qquad (9)$$

Next, an average value of the current velocity obtained by Equation (9) and the velocity obtained in the past, and a position obtained last time are used to compute the following Equation (10), and the position in the E frame is obtained.

$$r_{eb}^e(t+\tau_i) \approx r_{eb}^e(t) + \frac{1}{2}(v_{eb}^e(t) + v_{eb}^e(t+\tau_i))\tau_i \qquad (10)$$

5. Comparative Example

Figure 10:
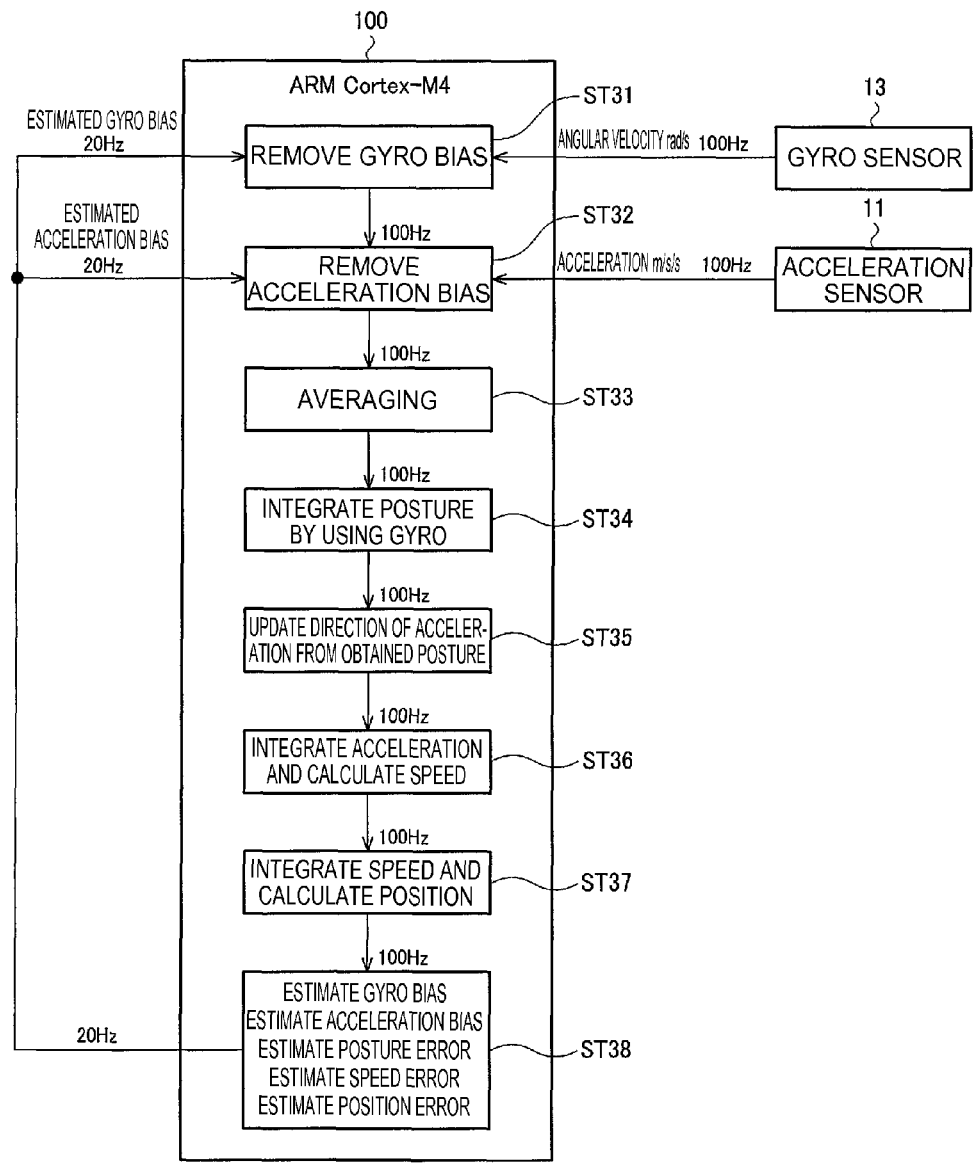
FIG. 10 is a flowchart illustrating operations in a comparative example.

FIG. 10 is a flowchart illustrating operations in a comparative example. In the comparative example shown in FIG. 10, the acceleration sensor 11 and the gyro sensor 13 input an acceleration and an angular velocity at the same frequency (500 Hz in FIG. 10) to the processing unit 100.

Here, in the case where the processing unit 100 shown in FIG. 10 performs all the operations including an operation of computing the posture by integrating the angular velocity and calculation of the position at a frequency of 500 Hz, for example, the processing burden on the processing unit 100 is heavier than in the case where the computation is performed at the second frequency f2=20 Hz as in the embodiment.

As a comparison example for a method of reducing the burden on the processing unit 100, averaging will be described. As in the following Equation (11), angular velocities of a plurality of data items (plurality of cycles) are added up without being multiplied. This will be referred to as averaging. As represented by Equation (11), angular velocities during a predetermined period (from $\tau_3$ to $n\tau_3$) are added instead of calculating one coordinate transformation matrix for each first cycle $\tau_1$, and the obtained matrix is used to calculate a coordinate transformation matrix. Since angular velocities for n=five cycles are averaged in the comparative example, the computation after the calculation of exp (α) is performed at f=100 Hz, and the calculation burden can be reduced. In Equation (11), $\tau_3$ represents a third cycle and satisfies $\tau_3=1/f$.

$$C_b^e(t+n\tau_3)=C_b^e(t)\exp([\alpha_{ib}^b(t+\tau_3)+\alpha_{ib}^b(t+2\tau_3)+ \ldots +\alpha_{ib}^b(t+5\tau_3)]\times) \quad (11)$$

The averaging in Equation (11) can be preferably used without causing a large error in a case where a vehicle or the like whose variation in angular velocity for a short time is relatively small is the moving object. However, in the case of the moving object which performs walking motion as in the embodiment, the variation in angular velocity is relatively large, and therefore, it was found that a large error was generated in the averaging and that accuracy of the posture calculation was insufficient.

FIGS. 11 to 16 are diagrams illustrating errors of the position of the moving object, which are calculated in the example of the embodiment and the comparative example. In FIGS. 11 to 16, simulation of moving from a start point (0, 0) as shown by the arrow in the drawing and returning to an endpoint (0, 0) is performed on the two-dimensional position coordinates (X, Y), and the position is calculated. In each of the drawings, the vertical axis and the horizontal axis represent position coordinates. The unit is in meters. The broken line represents a true value of a track, a one-dotted chain line represents a result of the embodiment, and a solid line represents a result of the comparative example. In the embodiment employed in FIGS. 11 to 13, the first frequency f1=7.81 kHz, and the second frequency f2=100 Hz. In contrast, in the comparative example employed in FIGS. 11 to 13, the posture computation is performed at f=100 Hz by averaging the angular velocities detected at the frequency of 7.81 kHz. A human is assumed as the moving object, and cases where the human moves in three methods, namely dashing (sprinting), running (galloping), and walking are compared.

Figure 11:
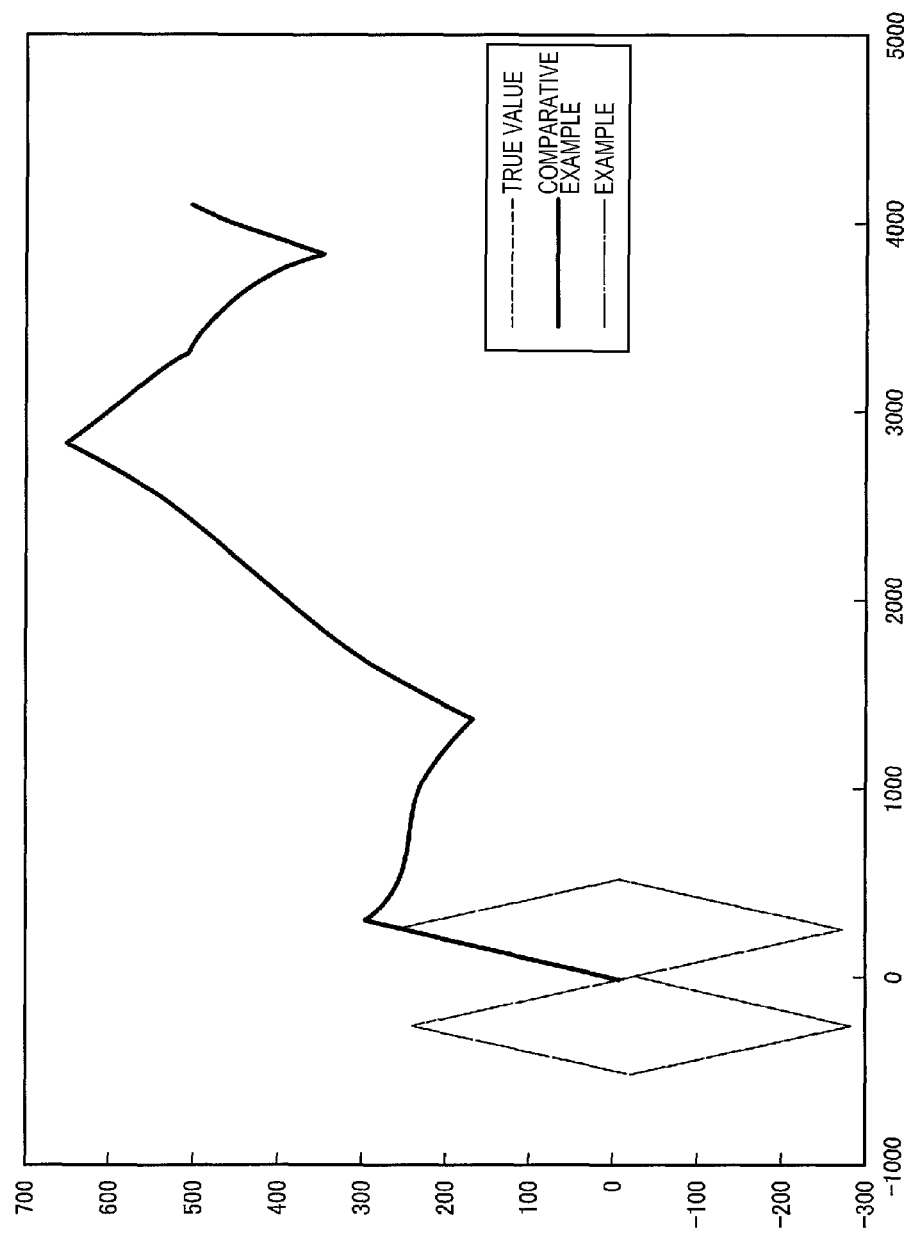
FIG. 11 is a diagram illustrating an error which is generated when a position of a dashing moving object is calculated according to the embodiment and the comparative example.
Figure 12:
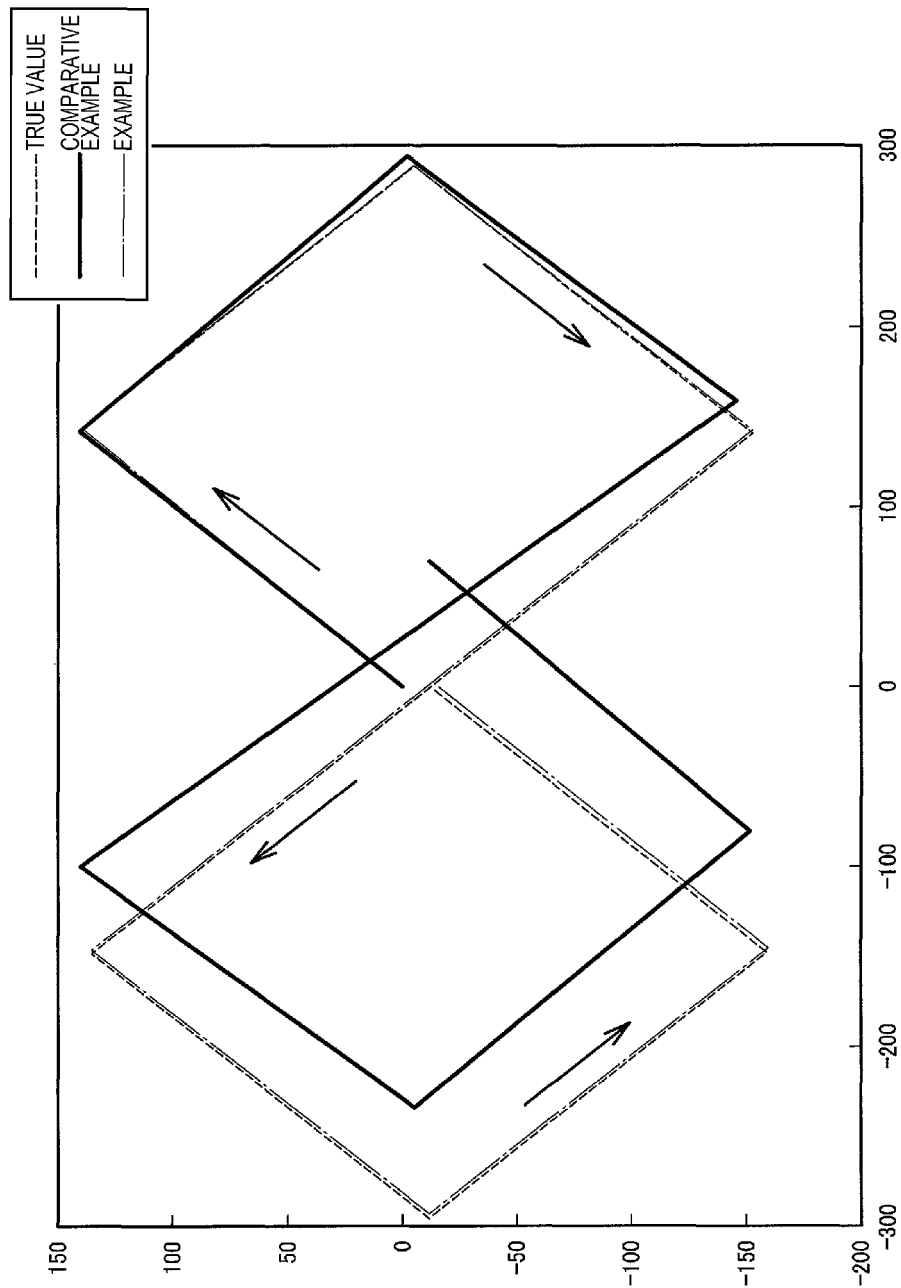
FIG. 12 is a diagram illustrating an error which is generated when a position of a running moving object is calculated according to the embodiment and the comparative example.
Figure 13:
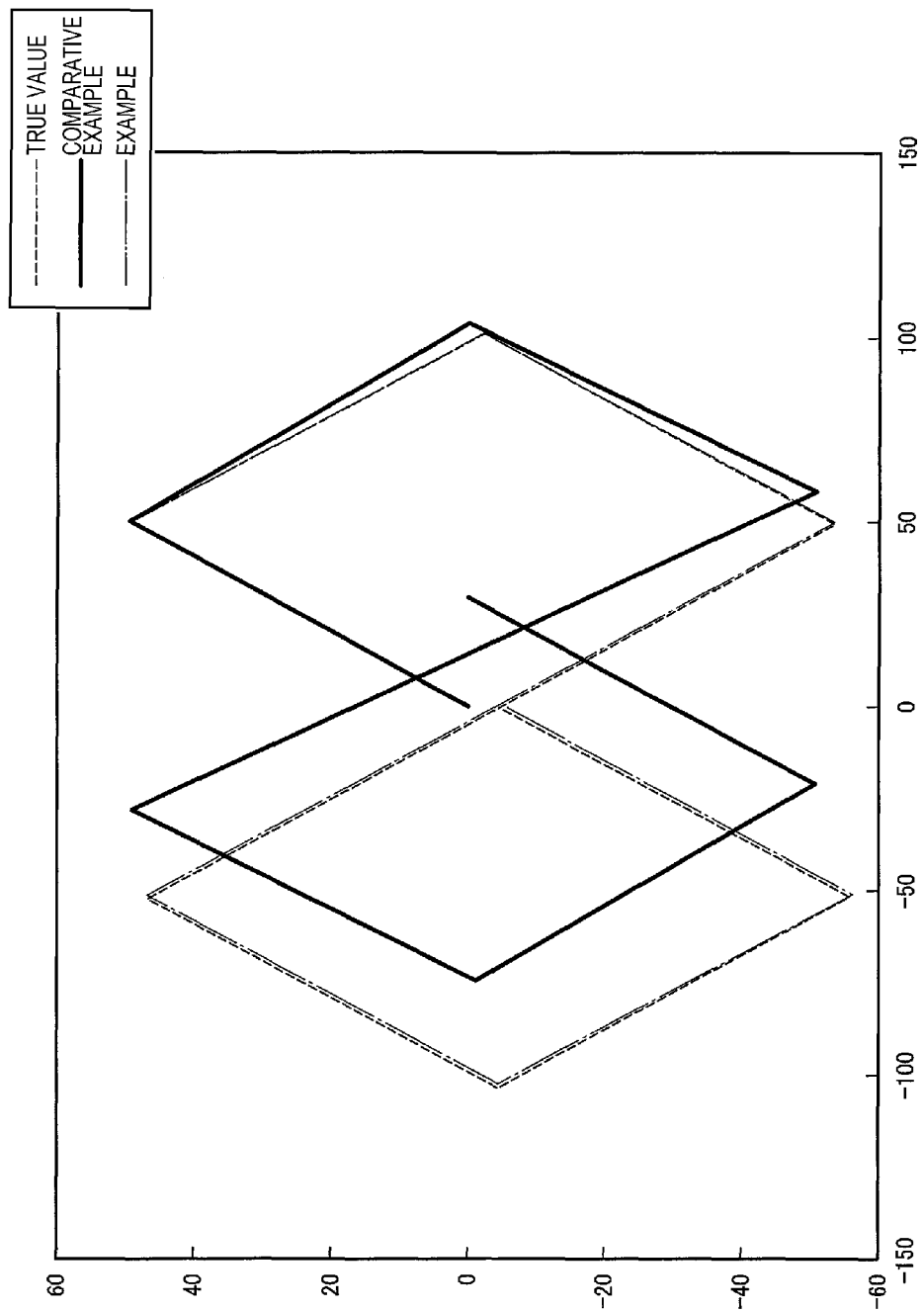
FIG. 13 is a diagram illustrating an error which is generated when a position of a walking moving object is calculated according to the embodiment and the comparative example.

FIG. 11 shows an example where the moving object dashes and moves, FIG. 12 shows an example where the moving object runs and moves, and FIG. 13 shows an example where the moving object walks and moves. In FIGS. 11 to 13, the calculation results according to the embodiment substantially coincide with the true value, and substantially no error occurs. In contrast, all the calculation results according to the comparative example include large errors, and in FIG. 11 in which the variation in angular velocity is large, a calculation result with substantially no reproducibility is obtained.

Figure 14:
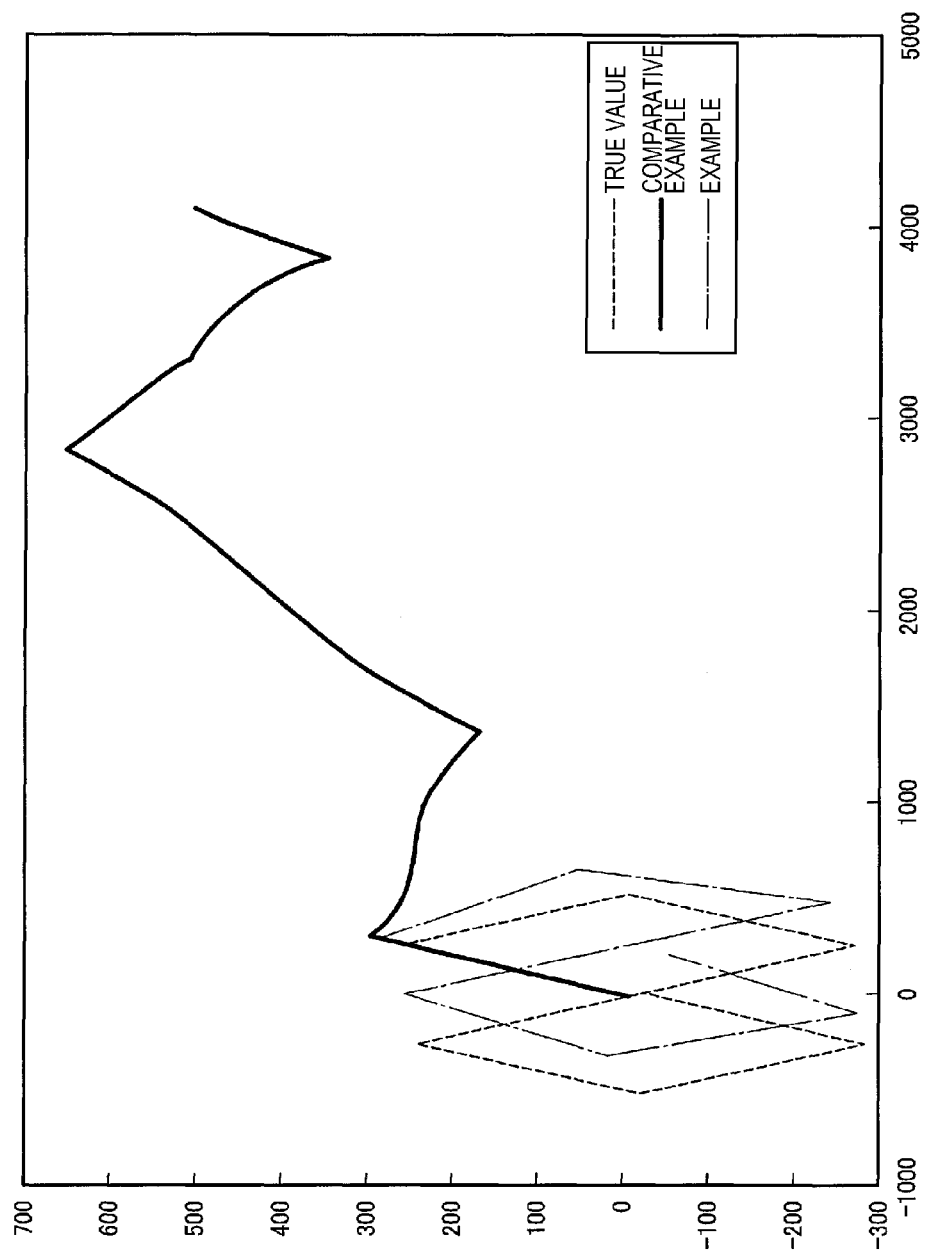
FIG. 14 is a diagram showing a comparison result under the same condition as that in FIG. 11 except that a second frequency is lowered.
Figure 15:
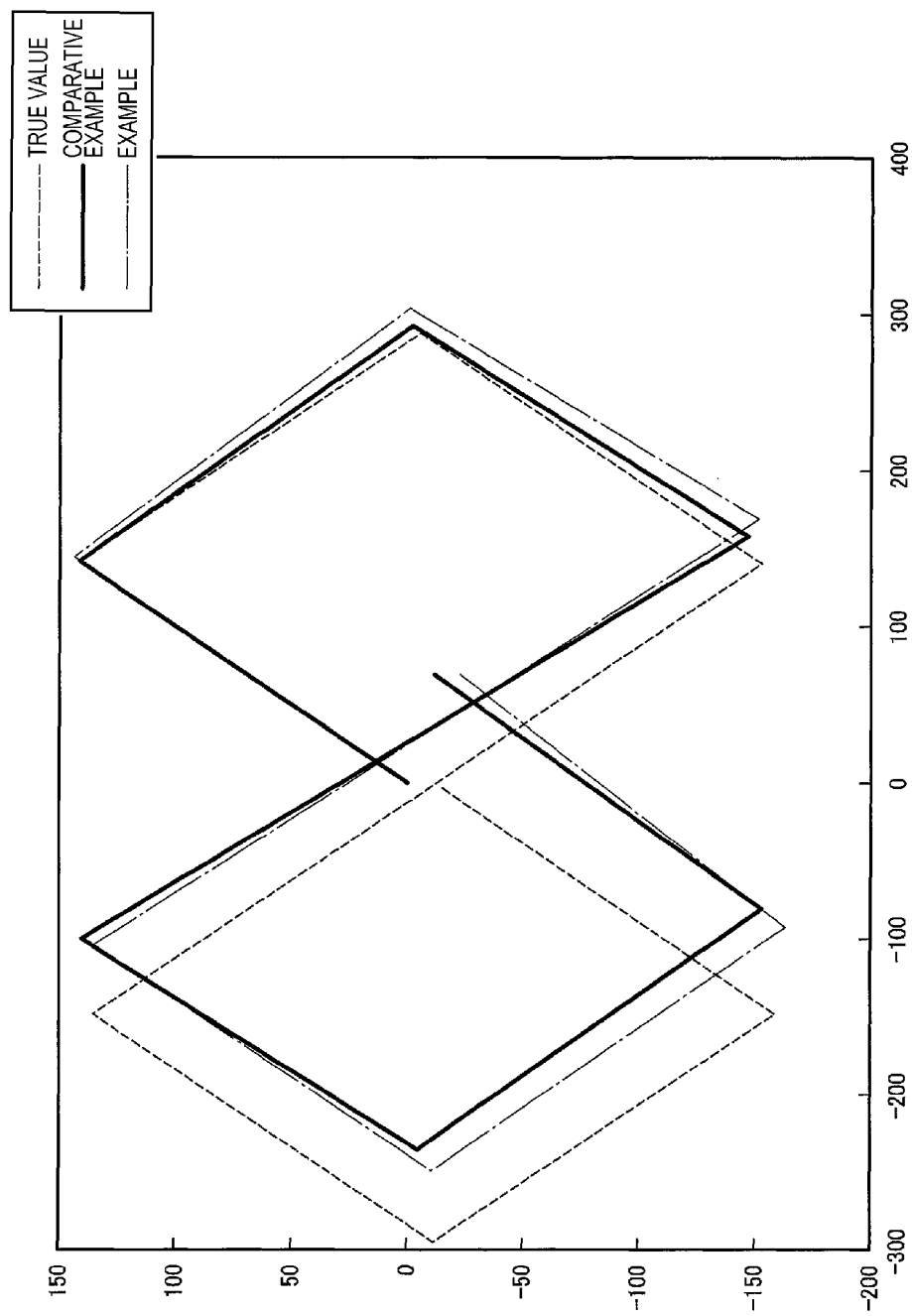
FIG. 15 is a diagram showing a comparison result under the same condition as that in FIG. 12 except that the second frequency is lowered.
Figure 16:
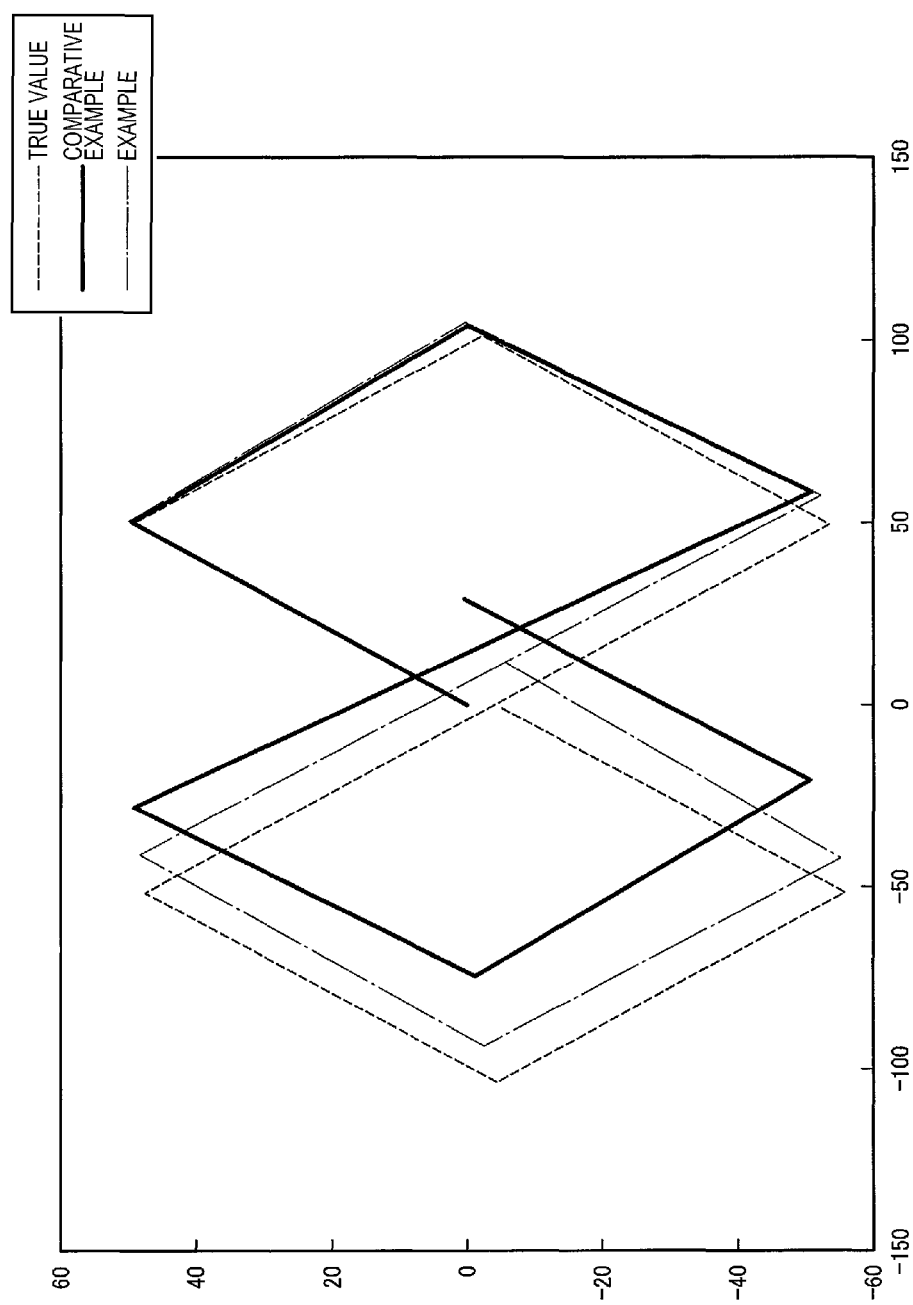
FIG. 16 is a diagram showing a comparison result under the same condition as that in FIG. 13 except that the second frequency is lowered.

In the embodiment employed in FIGS. 14 to 16, the first frequency f1=7.81 kHz, and the second frequency f2=20 Hz. In contrast, in the comparative example employed in FIGS. 14 to 16, the posture computation is performed at f=100 Hz by averaging the angular velocities detected at the frequency of 7.81 kHz in the same manner as in FIGS. 11 to 13.

FIG. 14 shows an example where the moving object dashes and moves, FIG. 15 shows an example where the moving object runs and moves, and FIG. 16 shows an example where the moving object walks and moves. As a result of setting the second frequency f2 to be low, the calculation results according to the embodiment shown in FIGS. 14 to 16 include larger errors than those in FIGS. 11 to 13. However, it is possible to understand that the errors are smaller than those in the comparative example in which the calculation is performed at the frequency of 100 Hz that is higher than that in the embodiment. As can be understood from FIG. 16, it is possible to sufficiently reproduce the motion of the moving object even if the second frequency f2 is a value which is as low as 20 Hz in a case of the variation in angular velocity in the level of walking. Therefore, according to the embodiment, it is possible to suppress the computation burden and to appropriately calculate the posture of the moving object by updating the posture so as to satisfy f1>f2≥20 Hz.

6. Modification Example

It is a matter of course that embodiments to which the invention can be applied are not limited to the above first to third embodiments and various modifications can be appropriately made without departing from the gist of the invention. Hereinafter, a description will be given of modification examples. In addition, the same reference numerals will be given to the same configuration as those in the above embodiments, and repeated descriptions will be omitted.

6-1. Overall Configuration of System

Figure 17:
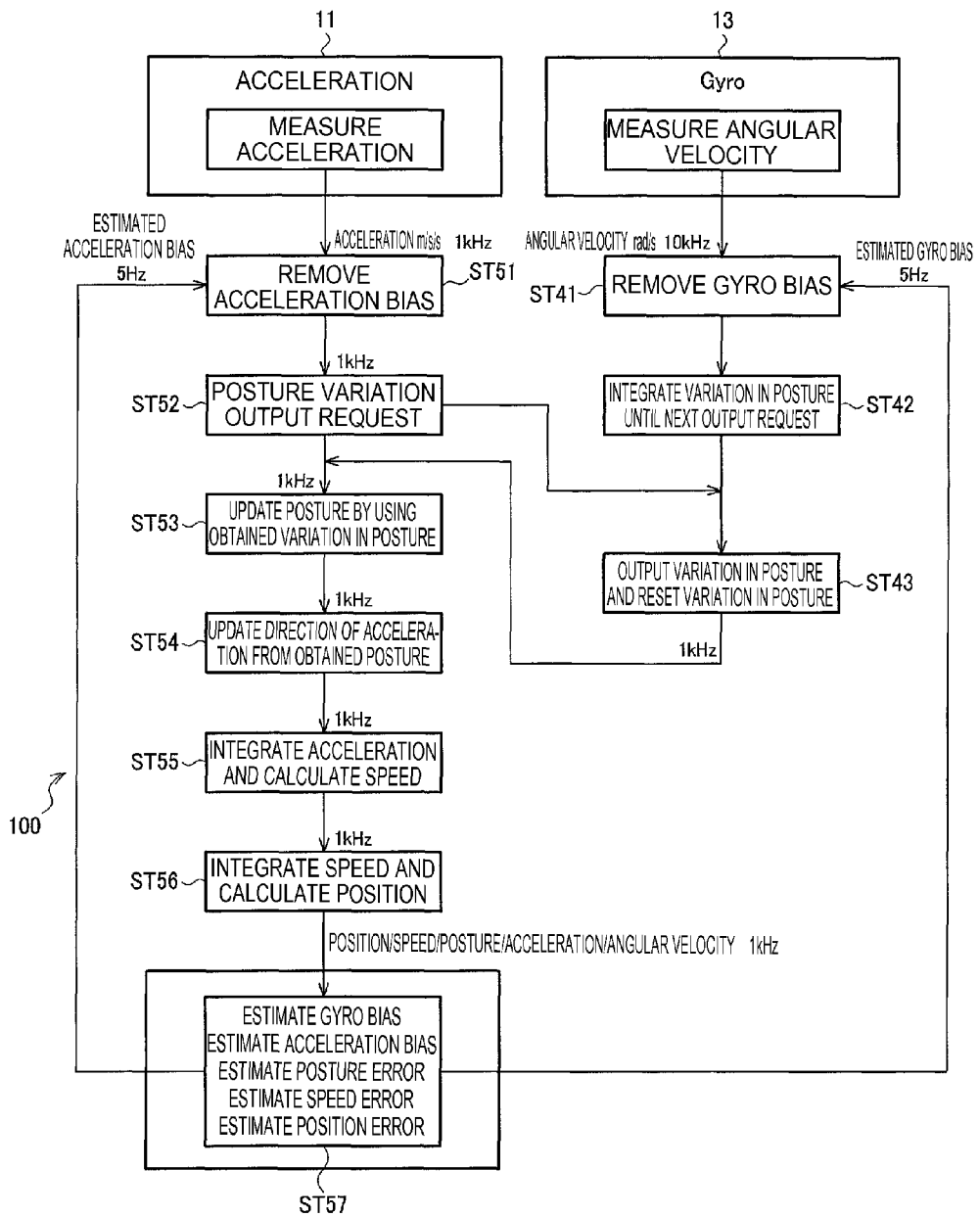
FIG. 17 is a diagram showing an operation flowchart of a modification example in which a main function of the processing unit is implemented by hardware.

FIG. 17 is an operation flowchart according to a modification example in which the functional block of the gyro sensor IC shown in FIG. 3 is taken into the processing unit 100 and main functions of the processing unit are implemented by hardware. Here, ST41 to ST43 shown in FIG. 17 are the same as ST12 to ST14 in FIG. 4. In addition, ST51 to ST57 shown in FIG. 17 are the same as ST21 and ST23 to ST28 shown in FIG. 4 (the operation corresponding to ST22 is omitted). Since the content itself of the computation is the same as that in the embodiment in FIG. 4, the description will be omitted, and only a different part from that in the embodiment in FIG. 4 will be described. In FIG. 17, the first frequency f1=10 kHz, the second frequency f2=1 kHz, the third frequency f3=1 kHz, and the acceleration averaging unit 123 shown in FIG. 3 is not necessary. Since the posture variation calculating unit 113 is implemented as hardware in the same manner as in the aforementioned embodiments, it is possible to perform the heavy computation by the hardware without applying a burden on the CPU even in this case.

In addition, since the posture updating unit 124 is also implemented as hardware, it is possible to set the second frequency f2 to satisfy f2=1 kHz, which is significantly higher than the second frequency f2=20 Hz in the aforementioned embodiments, and to update the posture with high accuracy.

6-2. Posture Calculating Apparatus

Although the example in which the position calculating apparatus 1 including the function of the posture calculating apparatus was described in the aforementioned embodiments, the posture calculating apparatus may be configured as an independent apparatus. For example, it is possible to configure the posture calculating apparatus as a device including the gyro sensor 13, the gyro sensor IC 14, and the posture updating unit 124.

6-3. Posture Variation Calculating Unit

Although the example in which the posture variation calculating unit 113 was implemented as hardware was described in the aforementioned embodiment, the posture variation calculating unit 113 can be configured as software. In such a case, the posture variation calculating unit 113 may be configured as a part of the processing unit 100.

6-4. GPS Unit

Although the example in which the position calculating apparatus 1 was provided with the GPS unit 15 was described in the aforementioned embodiments, the GPS unit may be omitted.

6-5. Moving Object

Although the example in which the moving object was a human was described in the aforementioned embodiments, the moving object is not limited to a human. In a case where an error of a posture or a position calculated by applying averaging is not allowable, it is possible to achieve an effect by applying the invention. For example, the living object may be an animal other than a human. The motion of the moving object is not limited to walking and running and may be jumping, swimming, sliding, flying, or the like. Examples of the moving object which moves by using energy of a living object as a power source include skate boards, skate shoes, a bicycle, a hang glider, a boat, and a sleigh. The IMU 10 may be mounted on a living object or a moving object which moves by using the energy of the living object as a power source.

Those skilled in the art will easily understand that multiple modifications can be made without substantially departing from the new matters and effects of the invention. Therefore, all the modifications are included in the scope of the invention. For example, a term which is replaced with a different term with wider or similar meaning at least once in the specification or the drawing can be replaced with a different term at any location in the specifications or the drawings. In addition, the first and second coordinate systems are not limited to three-dimensional coordinate systems and may be two-dimensional coordinate systems.

The entire disclosure of Japanese Patent Application No. 2013-233372, filed Nov. 11, 2013 is expressly incorporated by reference herein.

What is claimed is:

1. An integrated circuit (IC) comprising:
   an analog circuit configured to (i) receive, from a gyro sensor, an analog signal that is generated based on an angular velocity applied to the gyro sensor and (ii) amplify the analog signal;
   an analog-to-digital (AD) conversion unit configured to convert the analog signal from the analog circuit into a digital signal;
   a posture variation calculating unit configured to (i) calculate a variation in posture of the gyro sensor during a predetermined integration period based on the digital signal from the AD conversion unit and (ii) output the calculated variation in posture;
   an interface unit configured to receive a command signal from a host terminal; and
   a control unit configured to control the posture variation calculating unit based on the command signal received from the interface,
   wherein the control unit is further configured to set, based on the command signal, a start and an end of calculating the variation in posture of the gyro sensor in accordance with the predetermined integration period.

2. The IC according to claim 1,
   wherein the AD conversion unit is further configured to convert the analog signal from the analog circuit into the digital signal at a first frequency f1,
   the posture variation calculating unit is further configured to output the calculation variation in posture at a second frequency f2 which is less than f1, and
   the posture variation calculating unit is further configured to compute $\exp([\alpha_{ib}^{b}(t+\tau_1)]\times)\exp([\alpha_{ib}^{b}(t+2\tau_1)]\times) \ldots \exp([\alpha_{ib}^{b}(t+k\tau_1)]\times)$ where $\tau_1=1/f1$, k is an integer which satisfies (f1/f2)−1<k≤f1/f2, t represents a time, and $[\alpha_{ib}^{b}(t+n\tau_1)]$ represents a rotation matrix acquired from the angular velocity at a time $t+n\tau_1$ (n is an integer which satisfies 1≤n≤k).

3. The IC according to claim 1, further comprising:
   a command decoder configured to decode the command signal input from the outside; and
   a register configured to store a value for controlling the posture variation calculating unit based on a decoding result of the command decoder.

4. The IC according to claim 3,
   wherein the command decoder is further configured to set a start and an end of the calculating operation by the posture variation calculating unit in the register based on the command signal.

5. The IC according to claim 2,
   wherein the posture variation calculating unit includes an adder and a multiplier configured to perform approximating operation of $\exp([\alpha(t+n\tau_1)]\times)$.

6. The IC according to claim 1,
   wherein the control unit is further configured to set an approximation function order as a control value for the posture variation calculating unit.

7. The IC according to claim 1,
   wherein the control unit is further configured to set a bias updating timing as a control value for the posture variation calculating unit.

8. The IC according to claim 1,
   wherein the control unit is further configured to set an angular velocity conversion coefficient as a control value for the posture variation calculating unit.

9. The IC according to claim 1,
   wherein the control unit is further configured to set a bias estimated value as a control value for the posture variation calculating unit.

10. The IC according to claim 1,
    wherein the control unit is further configured to set a sampling rate as a control value for the posture variation calculating unit.

* * * * *